United States Patent
Dudek et al.

(10) Patent No.: US 6,686,388 B2
(45) Date of Patent: *Feb. 3, 2004

(54) REGULATORS OF THE HEDGEHOG PATHWAY, COMPOSITIONS AND USES RELATED THERETO

(75) Inventors: Henryk Dudek, Wellesley, MA (US); Benxiu Ji, Sharon, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/867,311

(22) Filed: May 29, 2001

(65) Prior Publication Data

US 2001/0034337 A1 Oct. 25, 2001

Related U.S. Application Data

(63) Continuation of application No. 09/417,564, filed on Oct. 14, 1999, now Pat. No. 6,291,516.
(60) Provisional application No. 60/115,642, filed on Jan. 13, 1999, provisional application No. 60/119,544, filed on Feb. 10, 1999, and provisional application No. 60/142,124, filed on Jul. 2, 1999.

(51) Int. Cl.[7] ............... A61K 31/335; G01N 33/574; G01N 33/50; G01N 33/483; C12N 15/00
(52) U.S. Cl. .......... 514/455; 514/47; 514/573; 514/169; 514/605; 514/222.5; 514/226.2; 514/236.2; 514/617; 514/620; 514/642; 514/651; 514/652; 514/653; 514/863; 514/257; 514/258; 514/260; 514/261; 514/262; 514/263; 514/266; 514/275; 514/280; 514/311; 514/314; 514/317; 514/327; 514/331; 514/346; 514/347; 514/397; 514/415; 514/420; 514/424; 514/470; 514/473; 514/478
(58) Field of Search ............... 514/455, 47, 169, 514/222.5, 226.2, 236.2, 257, 258, 260, 261, 262, 263, 266, 275, 280, 311, 314, 317, 327, 331, 346, 347, 397, 415, 420, 424, 470, 473, 478, 479, 523, 530, 535, 537, 538; 424/236.1, 240.1; 600/562

(56) References Cited

U.S. PATENT DOCUMENTS

| 4,007,268 A | 2/1977 | Voorhees ............... 424/200 |
| 4,353,888 A | 10/1982 | Sefton ............... 424/25 |
| 4,634,706 A | 1/1987 | Kaneko et al. ............... 514/262 |
| 4,751,224 A | 6/1988 | Agarwal et al. ............... 514/248 |

(List continued on next page.)

FOREIGN PATENT DOCUMENTS

| EP | 0020029 A1 | 10/1980 | ............ C07J/71/00 |
| WO | WO 89/11487 | 11/1989 | ......... C07H/19/167 |
| WO | WO 91/07087 | 5/1991 | ............ A01N/1/02 |
| WO | WO 91/10743 | 7/1991 | ............ C12Q/1/02 |
| WO | WO 93/09668 | 5/1992 | ............ A01N/1/02 |

(List continued on next page.)

OTHER PUBLICATIONS

Murone et al., Sonic Hedgehog Signaling by the Patched–Smoothened Receptor Complex, Jan. 12, 1999, Current Biology, vol. 9, pp. 76–84.*

(List continued on next page.)

*Primary Examiner*—Frederick Krass
*Assistant Examiner*—Clinton Ostrup
(74) *Attorney, Agent, or Firm*—Ropes & Gray LLP

(57) ABSTRACT

The present invention makes available methods and reagents for inhibiting aberrant growth states resulting from hedgehog gain-of-function, ptc loss-of-function or smoothened gain-of-function comprising contacting a cell with a compound, such as a polypeptide or small molecule in an amount sufficient to control the aberrant growth state e.g., to agonize a normal ptc pathway or antagonize smoothened or hedgehog activity. The present invention further makes available methods and reagents for ameliorating to consequences of hedgehog loss-of-function, ptc gain-of-function, or smoothened loss-of-function comprising contacting a cell with a compound, such as a polypeptide or small molecule, in an amount sufficient to ameliorate the In certain embodiments, the subject compounds, e.g., a cAMP analog, adenylate cyclase agonist, or cAMP phosphodiesterase inhibitor, regulate cAMP levels, which in turn modulates activity of the hedgehog pathway.

14 Claims, 19 Drawing Sheets

U.S. PATENT DOCUMENTS

| | | | |
|---|---|---|---|
| 4,892,538 A | 1/1990 | Aebischer et al. | 604/891.1 |
| 4,955,892 A | 9/1990 | Daniloff | 606/152 |
| 5,041,138 A | 8/1991 | Vacanti et al. | 623/16 |
| 5,092,871 A | 3/1992 | Aebischer et al. | 606/152 |
| 5,288,514 A | 2/1994 | Ellman | 427/2 |
| 5,359,115 A | 10/1994 | Campbell et al. | 558/110 |
| 5,362,899 A | 11/1994 | Campbell | 558/108 |
| 5,565,462 A | 10/1996 | Eitan et al. | 514/262 |
| 5,712,171 A | 1/1998 | Zambias et al. | 436/518 |
| 5,736,412 A | 4/1998 | Zambias et al. | 436/518 |
| 5,789,439 A | 8/1998 | Hosono et al. | 514/455 |
| 6,291,516 B1 * | 9/2001 | Dudek et al. | 514/455 |

FOREIGN PATENT DOCUMENTS

| | | | |
|---|---|---|---|
| WO | WO 92/10092 | 6/1992 | A01N/1/02 |
| WO | WO 93/01275 | 1/1993 | C12N/5/00 |
| WO | WO 93/20242 | 10/1993 | C12Q/1/70 |
| WO | WO 93/21929 | 11/1993 | A61K/31/70 |
| WO | WO 94/08051 | 4/1994 | C12Q/1/68 |
| WO | WO 94/09229 | 4/1994 | E04G/17/06 |
| WO | WO 94/10292 | 5/1994 | C12N/5/06 |
| WO | WO 94/16718 | 8/1994 | A61K/37/00 |
| WO | WO 98/58650 | 12/1998 | A61K/31/56 |
| WO | WO 99/52534 | 10/1999 | A61K/31/585 |

OTHER PUBLICATIONS

Epstein et al., Antagonizing cAMP–dependent Protein Kinase A in the Dorsal CNS Activates a Conserved Sonic Hedgehog Signaling Pathway, 1996, Development, vol. 122, pp. 2885–2894.*

Alcedo et al. "The drosophila smoothened gene encodes a seven–pass membrane protein, a putative receptor for the hedgehog signal." *Cell*, 86: 221–232 (1996).

Altaba. "Restrictions to floor plate induction by hedgehog and winged–helix genes in the neuroal tube of frog embryos." *Mol. Cell. Neurosci.*, 6: 106–121 (1995).

Apelqvist et al. "Sonic hedgehog directs specialised mesoderm differentiation in the intestine and pancreas." *Curr. Biol.*, 7:801–804 (1997).

Bellusci et al. "Involvement of Sonic hedgehog in mouse embryonic lung growth and morphogenesis." *Development*, 124:53 (1997).

Berge et al. "Pharmaceutical Salts." *J. Pharm Sci*, 66:1–19 (1977).

Bitgood et al. "Sertoli cell signaling by Desert hedgehog regulates the male germline." *Curr. Biol.*, 6:298 (1996).

Bitgood and MacMahon. "Hedgehog and Bmp Genes are coexpressed at many diverse sites of cell–cell interaction in the mouse embryo." *Dev. Biol.*, 172:126–138 (1995).

Bumcrot et al. "Proteolytic processing yields two secreted forms of sonic hedgehog." *Mol. Cell. Biol.*, 15:2294–2303 (1995).

Chang et al. "Products, genetic linkage and limb patterning activity of a murine hedgehog gene." *Development*, 120:3339–3353 (1994).

Chen et al. "Analogous'organic synthesis of small–compound libraries: validation of combinatorial chemistry in small–molecule synthesis." *JACS*, 116:2661 (1994).

Chen et al. "Dual roles for patched in sequestering and transducing hedgehog." *Cell*, 87:553–563 (1996).

Davidson, E. "How embryos work: a comparative view of diverse modes of cell fate specification." *Development* 108: 365–389 (1990).

Dunnett et al. "Mechanisms of function of neural grafts in the adult mammalian brain." *J. Exp. Biol.*, 132:265–289 (1987).

Echelard et al. "Sonic hedgehog, a member of a family of putative signaling molecules, is implicated in the regulation of CNS polarity." *Cell*, 75:1417–1430 (1993).

Ekker et al. "Patterning activities of vertebrate hedgehog proteins in the developing eye and brain." *Curr. Biol.*, 5:944–955 (1995).

Ekker et al. Distinct expression and shared activities of members of the hedgehog gene family of xenopus laevis. *Development*, 121:2337–2347 (1995).

Ericson et al. "Sonic hedgehog induces the differentiation of ventral forebrain neurons: a common signal for ventral patterning within the neural tube." *Cell*, 81:747–756 (1995).

Fan and Tessier–Lavigne: Patterning of Mammalian Somites by Surface Ectoderm and Notochord: Evidence for Scherotome Induction by Hedgehog Homolog, *Cell*, 79:1175–1186 (1994).

Fan et al. "Long–Range sclerotome induction by sonic hedgehog: direct role of the amino–terminal cleavage product and modulation by the cyclic AMP signaling pathway." *Cell*, 81:457–465 (1995).

Fietz et al. "Secretion of the amino–terminal fragment of the hedgehog protein is necessary and sufficient for hedgehog signalling in drosophia." *Curr. Biol.*, 5:643–651 (1995).

Forbes et al. "Hedgehog is required for the proliferation and specification of ovarian somatic cells prior to egg chamber formation in Drosophial." *Development*, 122:1125–1135 (1996).

Francis et al. "Bone morphogenetic proteins and a signalling pathway that controls patterning in the developing check limb." *Development*, 120:209–218 (1994).

Freed et al. "Neocartilage formation in vitro and in vivo using cells cultured on synthetic biodegradable polymers." *J. Biomed Mater Res*, 27:11–23 (1993).

Freund et al. "Efferent synaptic connections of grafted dopaminergic neuorons reinnervating the host neostriatum: a tyrosine hydroxylase imminocytochemical study." *J. Neuroscience*, 5:603–616 (1985).

Fujita et al. "Involvement of Sonic hedgehog in the cell growth of LK–2 cells, human lung squamous carcinoma cells." *Biochem Biophys Res Commun*, 238:658–664 (1997).

Gailani et al. "The role of the human homologue of Drosophila patched in sporadic basal cell carcinomas." *Nature Genetics*, 14:78–81 (1996).

Goodrich et al. "Altered neural cell fates and medulloblastoma in mouse patched mutants." *Science*, 277:1109–1113 (1997).

Goodrich et al. "Conservation of the hedgehog/patched signaling pathway from flies to mice: induction of a mouse patched gene by Hedgehog." *Genes Dev.* 10:301–312 (1996).

Grande et al. "The repair of experimentally produced defects in rabbit articular cartilage by autologous chondrocyte transplantation." *J Orthopaedic Res.*, 7:208–218 (1989).

Gurdon, "The Generation of Diversity and Pattern in Animal Development." *Cell*, 68: 185–199 (1992).

Hammerschmidt et al. "Protein kinase A is a common negative regulator of Hedgehog signaling in the vertebrate embryo." *Genes Dev.*, 10:647–658 (1996).

Hidalgo and Ingham. "Cell patterning in the Drosophila segment: spatial regulation of the segment polarity gene patched." *Development*, 110:291–301 (1990).

Hooper et al. "The drosophila patched gene encodes a putative membrane protein required for segmental patterning." *Cell*, 59: 751–764 (1989).

Hui et al. "Expression of three mouse homologs of the Drosophila segment polarity gene cubitus interruptus, Gli, Gli–2, and Gli–3, in ectoderm–and mesoderm–derived tissues suggests multiple roles during postimplantation development." *Dev Biol.*, 162:402–413 (1994).

Hynes et al. "Induction of Midbrain Dopaminergic Neurons by Sonic Hedgehog." *Neuron*, 15:35–44 (1995).

Jensen et al. "Expression of sonic hedgehog and its putative role as a precursor cell mitogen in the developing mouse retina." *Development*, 124:363 (1997).

Jessell. "Diffusible Factors in Vertebrate Embryonic Induction." *Cell*, 68: 257–270 (1992).

Johnson et al. "Ecotopic Expression of Sonic Hedgehog Alters Dorsal–Ventral Patterning of Somites" *Cell*, 79:1165–1173 (1994).

Johnson et al. "Human homolog of patched, a candidate gene for the basal cell nevus syndrome." *Science*, 272:1668–1671 (1996).

Kinzler et al. "The GLI gene encodes a nuclear protein which binds specific sequences in the human genome." *Mol. Cell. Biol.*, 10:634–642 (1990).

Krauss et al. "A functionally conserved homolog of the drosophila segment polarity gene hh is expressed in tissues with polarizing activity in zebrafish embryos." *Cell*, 75:1431–1444 (1993).

Lai et al.: "Patterning of the Neural Ectoderm of Xenopus laevis by the Amino–terminal Product of Hedgehog Autoproteolytic Cleavage", *Development*, 121:2349–2360 (1995).

Laufer et al. "Sonic hedgehog and Fgf–4 act through a signaling cascade and feedback loop to integrate growth and patterning of the developing limb bud." *Cell*, 79:993–1003 (1994).

Lee et al. "Autoproteolysis in hedgehog Protein Biogenesis." *Science*, 266:1528–1537 (1994).

Lee et al. "Secretion and Localized Transcription Suggest a Role in Positional Signaling for Products of the Segmentation Gene hedgehog." *Cell*, 71:33–50 (1992).

Lench et al. "Characterisation of human pateched germ line mutuations in naevoid basal cell carcinoma syndrome." *Human Genetic.*, 100 (5–6):497–502 (1997).

Levin et al. "A molecular pathway determining left–right asymmetry in chick embryogenesis." *Cell*, 82:803–814 (1995).

Lopez–Martinez et al. "Limb–patterning activity and restricted posterior localization of the amino–terminal product of Sonic hedgehog cleavage." *Curr. Biol.*, 5:791–795 (1995).

Marigo et al. "Biochemical evidence that Patched is the Hedgehog receptor." *Nature*, 384:177–179 (1996).

Marigo et al. "Conservation in hedgehog signaling: induction of a chicken pateched homolog by sonic hedgehog in the developing limb." *Development*, 122:1225–1233 (1996).

Marigo et al. "Regulation of patched by sonic hedgehog in the developing neural tube." *PNAS*, 93:9346–9351 (1996).

Marti et al. "Requirement of 19K form of Sonic hedgehog for induction of distinct ventral cell types in CNS explants." *Nature*, 375:322–325 (1995).

Marti' et al. "Distribution of sonic hedgehog peptides in the developing chick and mouse embryo." *Development*, 121:2537–2547 (1995).

Mitra–Kirtley et al. "Determination of the nitrogen chemical structures using XANES spectroscopy." *JACS*, 115:252–258 (1993).

Munsterberg et al. "Combinatorial signaling by Sonic hedgehog and Wnt family members induces myogenic bHLH gene expression in the somite." *Genes Dev.* 9:2911–2922 (1995).

Nakano et al. "A protein with several possible membrane–spanning domains encoded by Drosophila segment polarity gene patched." *Nature*, 341:508–513 (1989).

Niswander et al. "A positive feedback loop coordinates growth and patterning in the vertebrate limb." *Nature*, 371:609–612 (1994).

Nusse. "Patching up Hedgehog." *Nature*, 384:119–120 (1996).

Omnell et al. "Expression of Veratrum Alkaloid Teratogenicity in the Mouse." *Teratology*, 42:105–119 (1990).

Orenic et al. "Cloning and characterization of the segment polarity gene cubitus interruptus Dominant of Drosophila." *Genes and Development*, 4:1053–1067 (1990).

Oro et al. "Basal cell carcinomas in mice overexpressing sonic hedgehog." *Science* 276:817–821 (1997).

Perrimon. "Hedgehog and beyond." *Cell*, 80:517–520 (1995).

Perrimon. "Serpentine proteins slither into the wingless and hedgehog fields." *Cell*, 86:513–516 (1996).

Placzek et al. "Induction of floor plate differentiation by contract–dependent, homeogenetic signals." *Development*, 117:205–218 (1993).

Porter et al. "Hedgehog patterning activity: role of a lipophilic modification mediated by the carboxy–terminal auto-processing domain." *Cell* 86:21–34 (1996).

Porter et al. "The product of hedgehog autoproteolytic cleavage active in local and long–range signalling." *Nature*, 374:363–366 (1995).

Riddle et al. "Sonic hedgehog mediates the polarizing activity of the ZPA." *Cell*, 75:1401–1416 (1993).

Roberts et al. "Sonic hedgehog is an endodermal signal inducting BMP–4 and Hox genes during induction and regionalization of the chick hindgut." *Development*, 121:3163–3174 (1995).

Roelink et al. "Floor Plate and Motor Neuron Induction by Different Concentrations of the Amino–Terminal Cleavage Product of Sonic Hedgehog Autoproteolysis." *Cell*, 81:445–455 (1995).

Roelink et al. "Floor plate and motor neuron induction by vhh–1, a vertebrate homolog of hedgehog expressed by the notochord." *Cell*, 76:761–775 (1994).

Stone et al. "The tumour–suppressor gene patched encodes a candidate receptor for Sonic hedgehog." *Nature*, 384:129–134 (1996).

Stone et al.; "Future Directions", *Clin Orthop Relat Red*, 252:129 (1990).

Tabata et al. "The Drosophila hedgehog gene is expressed specifically in posterior compartment cells and is a target of engrailed regulation." *Genes Dev.*, 6: 2635–2645 (1992).

Takigawa et al. "Chondrocytes dedifferentiated by serial monolayer culture form cartilage nodules in nude mice." *Bone Miner*, 2:449 (1987).

Tanabe et al. "Induction of motor neurons by sonic hedgehog is independent of floor plate differentiation." *Curr Biol.*, 5:651–658 (1995).

Vacanti et al. "Synthetic polymers seeded with chondrocytes provide a template for new cartilage formation." *Plast Reconstr Surg,* 88:753 (1991).

von Schroeder et al. "The use of polyactic acid matrix and periosteal grafts for the reconstruction of rabbit knee articular defects." *J Biomed Mater Res,* 25:329 (1991).

Wakitani et al. "Repair of rabbit articular surfaces with allograft chondrocytes embedded in collagen cell." *J. Bone Jt Surg,* 71B:74 (1989).

Wang et al. "Induction of dopaminergic neuron phenotype in the midbrain by sonic hedgehog protein." *Nature Med.,* 1:1184–1188 (1995).

Weinberg et al. "Developmental regulation of zebrafish MyoD in Wild–type, no tail and spadetail embryos." *Development,* 122:271–280 (1996).

Xie et al.; "Mutations of the Patched Gene in Several Types of Sporadic Extracutaneous Tumors", *Cancer Res.,* 57:2369–2372 (1997).

Xie et al.; "Physically Mapping of the 5 Mb D9S196–D9S180 Interval Harboring the Basal Cell Nevus Syndrome Gene and Localization of Six Genes in This Region", *Genes Chromosomes Cancer,* 18:305–309 (1997).

Yamada et al. "Control of cell pattern in the neural tube: motor neuron induction by diffusible factors from notochord and floor plate." *Cell,* 73:673–686 (1993).

* cited by examiner

DMSO  Forskolin

REGULATORS OF THE HEDGEHOG PATHWAY, COMPOSITIONS AND USES RELATED THERETO

RELATED APPLICATIONS

This application is a Continuation of U.S. application Ser. No. 09/417,564, filed Oct. 14, 1999 now U.S. Pat. No. 6,291,516 which claims the benefit of U.S. Provisional Application No. 60/115,642, filed Jan. 13, 1999, U.S. Provisional Application No. 60/119,594, filed Feb. 10, 1999, and U.S. Provisional Application No. 60/142,124, filed Jul. 2, 1999, all hereby incorporated by reference in their entireties.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

Members of the Hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

The first hedgehog gene was identified by a genetic screen in the fruitfly *Drosophila melanogaster* (Nüsslein-Volhard, C. and Wieschaus, E. (1980) *Nature* 287, 795–801). This screen identified a number of mutations affecting embryonic and larval development. In 1992 and 1993, the molecular nature of the Drosophila hedgehog (hh) gene was reported (C. F., Lee et al. (1992) *Cell* 71, 33–50), and since then, several hedgehog homologues have been isolated from various vertebrate species. While only one hedgehog gene has been found in Drosophila and other invertebrates, multiple Hedgehog genes are present in vertebrates.

The vertebrate family of hedgehog genes includes at least four members, e.g., paralogs of the single drosophila hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedghog interacting proteins is of paramount significance in both clinical and research contexts.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33–50; Tabata, T. et al. (1992) *Genes Dev.* 2635–2645; Chang, D. E. et al. (1994) *Development* 120:3339–3353), Hedgehog precursor proteins undergo an internal autoproteolytic cleavage which depends on conserved sequences in the C-terminal portion (Lee et al. (1994) *Science* 266:1528–1537; Porter et al. (1995) *Nature* 374:363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294–2303; Porter et al. (1995) supra; Ekker, S. C. et al. (1995) *Curr. Biol.* 5:944–955; Lai, C. J. et al. (1995) *Development* 121:2349–2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Mart', E. et al. (1995) *Development* 121:2537–2547; Roelink, H. et al. (1995) *Cell* 81:445–455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21–34). Biochemical studies have shown that the autoproteolytic cleavage of the HH precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities in Drosophila and vertebrates (Porter et al. (1995) supra; Ekker et al. (1995) supra: Lai et al. (1995) supra; Roelink, H. et al. (1995) *Cell* 81:445–455; Porter et al. (1996) supra; Fietz, M. J. et al. (1995) *Curr. Biol.* 5:643–651; Fan, C. -M. et al. (1995) *Cell* 81:457–465; Mart', E., et al. (1995) *Nature* 375:322–325; Lopez-Martinez et al. (1995) *Curr. Biol* 5:791–795; Ekker, S. C. et al. (1995) *Development* 121:2337–2347; Forbes, A. J. et al.(1996) *Development* 122:1125–1135).

HH has been implicated in short- and long-range patterning processes at various sites during Drosophila development. In the establishment of segment polarity in early embryos, it has short-range effects which appear to be directly mediated, while in the patterning of the imaginal discs, it induces long range effects via the induction of secondary signals.

In vertebrates, several hedgehog genes have been cloned in the past few years. Of these genes, Shh has received most of the experimental attention, as it is expressed in different organizing centers which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) *Cell* 75:1417–1430), the rat (Roelink, H. et al. (1994) *Cell* 76:761–775) and the chick (Riddle, R. D. et al. (1993) *Cell* 75:1401–1416), and the shield in the zebrafish (Ekker et al. (1995) supra; Krauss, S. et al.(1993) *Cell* 75:1431–1444). In chick embyros, the Shh expression pattern in the node develops a left-right asymmetry, which appears to be responsible for the left-right situs of the heart (Levin, M. et al. (1995) *Cell* 82:803–814).

In the CNS, Shh from the notochord and the floorplate appears to induce ventral cell fates. When ectopically expressed, Shh leads to a ventralization of large regions of the mid- and hindbrain in mouse (Echelard et al. (1993) supra; Goodrich, L. V. et al. (1996) *Genes Dev.* 10:301–312), Xenopus (Roelink, H. et al. (1994) supra; Ruiz i Altaba, A. et al. (1995) *Mol. Cell. Neurosci.* 6:106–121), and zebrafish (Ekker et al. (1995) supra; Krauss et al. (1993) supra; Hammerschmidt, M., et al. (1996) *Genes Dev.* 10:647–658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Mart' et al. (1995) supra; Tanabe, Y. et al. (1995) *Curr. Biol.* 5:651–658). Moreover, antibody blocking suggests that Shh produced by the notochord is required for notochord-mediated induction of motor neuron fates (Mart' et al. (1995) supra). Thus, high concentration of Shh on the surface of Shh-producing midline cells appears to account for the contact-mediated induction of floorplate observed in vitro (Placzek, M. et al. (1993) *Development* 117:205–218), and the midline positioning of the floorplate immediately above the notochord in vivo. Lower concentrations of Shh released from the notochord and the floorplate presumably induce motor neurons at more distant ventrolateral regions in a process that has been shown to be contact-independent in vitro (Yamada, T. et al. (1993) *Cell* 73:673–686). In explants taken at midbrain and forebrain levels, Shh also induces the appropriate ventrolateral neuronal cell types, dopaminergic (Heynes, M. et al. (1995) *Neuron* 15:35–44; Wang, M. Z. et al. (1995) *Nature Med.* 1:1184–1188) and cholinergic (Ericson, J. et al. (1995) *Cell* 81:747–756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C. -M. and Tessier-Lavigne, M. (1994) *Cell* 79, 1175–1186).

Shh also induces myotomal gene expression (Hammerschmidt et al. (1996) supra; Johnson, R. L. et al. (1994) *Cell* 79:1165–1173; Münsterberg, A. E. et al. (1995) *Genes Dev.* 9:2911–2922; Weinberg, E. S. et al. (1996) *Development* 122:271–280), although recent experiments indicate that members of the WNT family, vertebrate homologues of Drosophila wingless, are required in concert (Münsterberg et al. (1995) supra). Puzzlingly, myotomal induction in chicks requires higher Shh concentrations than the induction of sclerotomal markers (Münsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) *Nature* 291:72–73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100–150 μm). Similar to the interaction of HH and DPP in the Drosophila imaginal discs, Shh in the vertebrate limb bud activates the expression of Bmp2 (Francis, P. H. et al. (1994) *Development* 120:209–218), a dpp homologue. However, unlike DPP in Drosophila, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) *Cell* 79:993–1003; Niswander, L. et al.(1994) *Nature* 371:609–612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) *Development* 121:3163–3174). Furthermore, Shh and Bmp2, 4, or 6 show a striking correlation in their expression in epithelial and mesenchymal cells of the stomach, the urogential system, the lung, the tooth buds and the hair follicles (Bitgood, M. J. and McMahon, A. P. (1995) *Dev. Biol.* 172:126–138). Further, Ihh, one of the two other mouse Hedgehog genes, is expressed adjacent to Bmp expressing cells in the gut and developing cartilage (Bitgood and McMahon (1995) supra).

Recent evidence suggests a model in which Indian hedgehog (Ihh) plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of Gli and Patched (Ptc), conserved transcriptional targets of Hedgehog signals (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Patched was originally identified in Drosophila as a segment polarity gene, one of a group of developmental genes that affect cell differentiation within the individual segments that occur in a homologous series along the anterior-posterior axis of the embryo. See Hooper, J. E. et al. (1989) Cell 59:751; and Nakano, Y. et al. (1989) Nature 341:508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) Cell 80:517; and Perrimon, N. (1996) Cell 86:513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, supra; Nakano, supra; Johnson, R. L. et al. (1996) Science 272:1668; and Hahn, H. et al. (1996) Cell 85:841. The biochemical role of patched in the hedgehog signaling pathway is unclear. Direct interaction with the hedgehog protein has, however, been reported (Chen, Y. et al. (1996) Cell 87:553), and patched may participate in a hedgehog receptor complex along with another transmembrane protein encoded by the smoothened gene. See Perrimon, supra; and Chen, supra.

The human homologue of patched was recently cloned and mapped to chromosome 9q22.3. See Johnson, supra; and Hahn, supra. This region has been implicated in basal cell nevus syndrome (BCNS), which is characterized by developmental abnormalities including rib and craniofacial alterations, abnormalities of the hands and feet, and spina bifida.

BCNS also predisposes to multiple tumor types, the most frequent being basal cell carcinomas (BCC) that occur in many locations on the body and appear within the first two decades of life. Most cases of BCC, however, are unrelated to the syndrome and arise sporadically in small numbers on sun-exposed sites of middle-aged or older people of northern European ancestry.

Recent studies in BCNS-related and sporadic BCC suggest that a functional loss of both alleles of patched leads to development of BCC. See Johnson, supra; Hahn, supra; and Gailani, M. R. et al. (1996) Nature Genetics 14:78. Single allele deletions of chromosome 9q22.3 occur frequently in both sporadic and hereditary BCC. Linkage analysis revealed that the defective inherited allele was retained and the normal allele was lost in tumors from BCNS patients.

Sporadic tumors also demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). The alterations did not occur in the corresponding germline DNA.

Most of the identified mutations resulted in premature stop codons or frame shifts. Lench, N. J., et al., Hum. Genet. 1997 October; 100(5–6): 497–502. Several, however, were point mutations leading to amino acid substitutions in either extracellular or cytoplasmic domains. These sites of mutation may indicate functional importance for interaction with extracellular proteins or with cytoplasmic members of the downstream signaling pathway.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

SUMMARY OF THE INVENTION

The present invention makes available methods and reagents for regulating aberrant activity of the hedgehog signaling pathway, such as hedgehog gain-of-function, ptc loss-of-function, smoothened gain-of-function, comprising contacting the cell with a ptc agonist, such as a steroidal alkaloid or other small molecule, in a sufficient amount to antagonize the hedgehog pathway, e.g., to agonize a normal ptc pathway or antagonize smoothened activity. The present invention also makes available methods and reagents for regulating aberrant activity of the hedgehog signaling pathway, such as hedgehog loss-of-function, ptc gain-of-function, smoothened loss-of-function, comprising contacting the cell with a ptc antagonist, such as a steroidal alkaloid or other small molecule, in a sufficient amount to antagonize the hedgehog pathway, e.g., to agonize a normal ptc pathway or antagonize smoothened activity.

Furthermore, in light of the discovery that increased levels of cyclic adenosine monophosphate (cAMP) deactivate the hedgehog signalling pathway to inhibit ptc loss-of-function, hedgehog gain-of-function, or smoothened gain-of-function, the present invention makes available methods and reagents which raise cAMP levels for inhibiting aberrant growth states resulting from activation of this pathway. Suitable compounds include compounds which interact with G-protein coupled receptors, adenylate cyclase agonists, cAMP analogs, and cAMP phosphodiesterase antagonists. The subject method comprises contacting the cell with one or more such agents, preferably small molecules, in an amount sufficient to reverse or control the aberrant growth state, e.g., to agonize a normal ptc pathway, antagonize a normal hedgehog pathway, or antagonize smoothened activity.

Alternatively, an agent which promotes decreased levels of cAMP may be employed to inhibit ptc gain-of-function, hedgehog loss-of-function, or smoothened loss-of-function may be used in methods and reagents for inhibiting aberrant growth states resulting from deactivation of the hedgehog pathway. Suitable compounds include compounds which interact with G-protein coupled receptors, adenylate cyclase antagonists, cAMP inhibitors, and cAMP phosphodiesterase agonists. The associated method comprises contacting a cell with one or more such agents, preferably small molecules, in an amount sufficient to reverse or control the aberrant growth state, e.g., to antagonize a normal ptc pathway, agonize a normal hedgehog pathway, or agonize smoothened activity.

In one embodiment, the invention relates to a method for inhibiting an altered growth state of a cell having a ptc loss-of-function phenotype or a smoothened gain-of-function phenotype, by contacting the cell with a ptc agonist in a sufficient amount to inhibit the altered growth state, wherein the ptc agonist is a organic molecule having a molecular weight less than about 750 amu.

In another embodiment, the invention relates to a method for inhibiting aberrant proliferation of a cell having a ptc loss-of-function phenotype or a smoothened gain-of-function phenotype by contacting the cell with a ptc agonist in a sufficient amount to inhibit proliferation of the cell.

In certain embodiments, the ptc agonist causes repression of smoothened-mediated signal transduction.

In certain embodiments, the ptc agonist is a steroidal alkaloid.

In certain embodiments, the steroidal alkaloid is represented in the general formulas (I), or unsaturated forms thereof and/or seco-, nor- or homo-derivatives thereof:

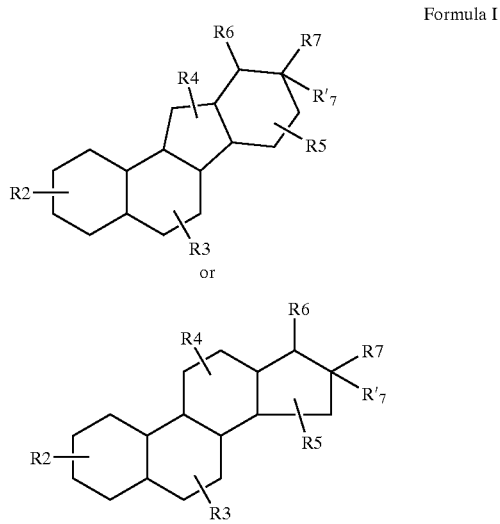

Formula I or wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —(CH$_2$)$_m$—R$_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle; and m is an integer in the range 0 to 8 inclusive.

In particular embodiments, $R_2$ and $R_3$, for each occurrence, is an —OH, alkyl, —O-alkyl, —C(O)-alkyl, or —C(O)—R$_8$;

$R_4$, for each occurrence, is an absent, or represents —OH, =O, alkyl, —O-alkyl, —C(O)-alkyl, or —C(O)—R$_8$;

$R_6$, $R_7$, and $R'_7$ each independently represent, hydrogen, alkyls, alkenyls, alkynyls, amines, imines, amides, carbonyls, carboxyls, carboxamides, ethers, thioethers, esters, or —(CH$_2$)$_m$—R$_8$, or $R_7$, and $R'_7$ taken together form a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle, and preferably $R_8$ is a piperidine, pyrimidine, morpholine, thiomorpholine, pyridazine, In certain embodiments, the steroidal alkaloid is represented in the general formula (II), or unsaturated forms thereof and/or seco-, nor- or homo-derivatives thereof:

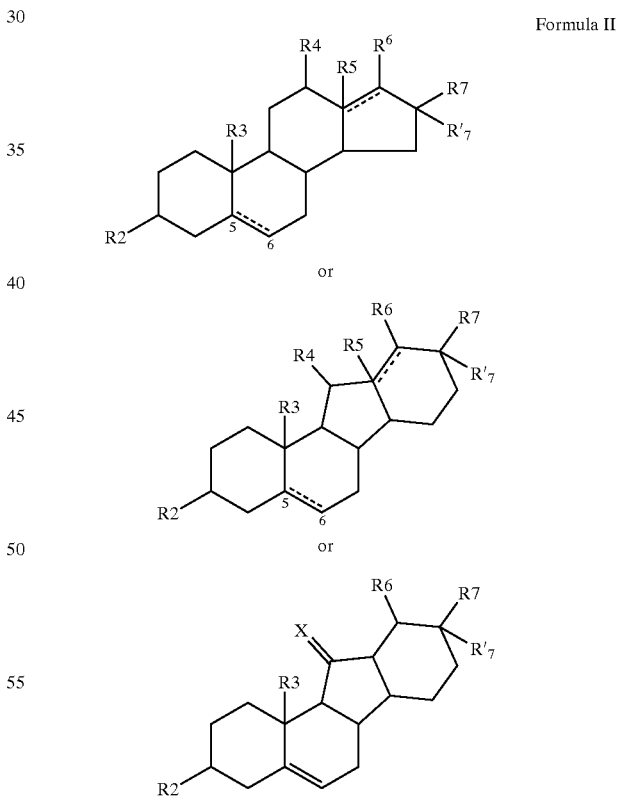

Formula II or or wherein $R_2$, $R_3$, $R_4$, $R_5$, $R_6$, $R_7$, and $R'_7$ are as defined above, and X represents O or S, though preferably O.

In certain embodiments, the steroidal alkaloid is represented in the general formula (III), or unsaturated forms thereof and/or seco-, nor- or homo-derivatives thereof:

Formula III

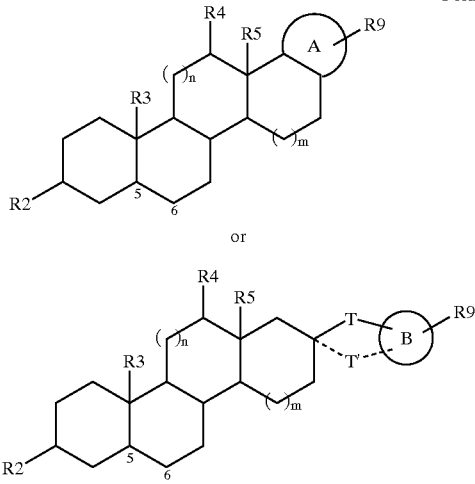

or wherein $R_2$, $R_3$, $R_4$, $R_5$ and $R_8$ are as defined above;

A and B represent monocyclic or polycyclic groups;

T represent an alkyl, an aminoalkyl, a carboxyl, an ester, an amide, ether or amine linkage of 1–10 bond lengths;

T' is absent, or represents an alkyl, an aminoalkyl, a carboxyl, an ester, an amide, ether or amine linkage of 1–3 bond lengths, wherein if T and T' are present together, than T and T' taken together with the ring A or B form a covelently closed ring of 5–8 ring atoms;

R9 represent one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or $-(CH_2)_m-R_8$; and n and m are, independently, zero, 1 or 2;

with the proviso that A and $R_9$, or T, T' B and $R_9$, taken together include at least one primary or secondary amine.

In certain embodiments, the steroidal alkaloid is represented in the general formula (IV), or unsaturated forms thereof and/or seco-, nor- or homo-derivatives thereof:

Formula IV

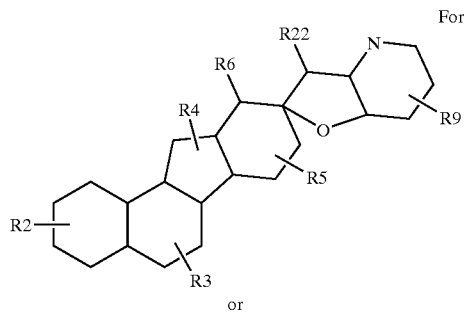

or

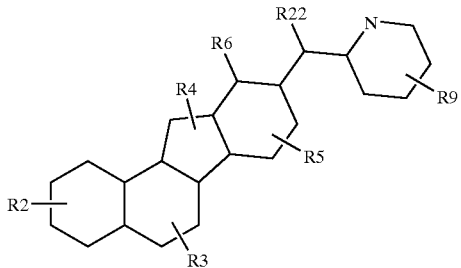

wherein $R_2$, $R_3$, $R_4$, $R_5$, $R_6$ and $R_9$ are as defined above;

$R_{22}$ is absent or represents an alkyl, an alkoxyl or —OH.

In certain embodiments, the steroidal alkaloid is represented in the general formula (V) or unsaturated forms thereof and/or seco-, nor- or homo-derivatives thereof:

Formula V

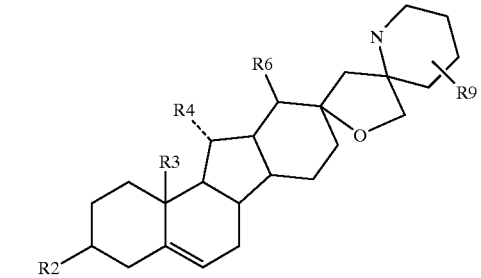

wherein $R_2$, $R_3$, $R_4$, $R_6$ and $R_9$ are as define above;

In certain embodiments, the steroidal alkaloid is represented in the general formula (VI), or unsaturated forms thereof and/or seco-, nor- or homo-derivatives thereof:

Formula VI

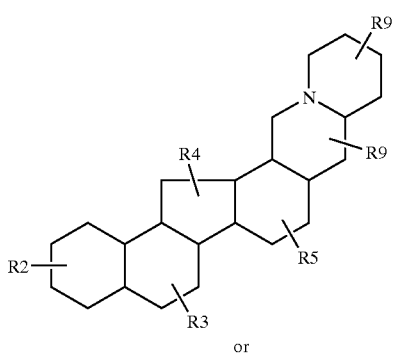

or

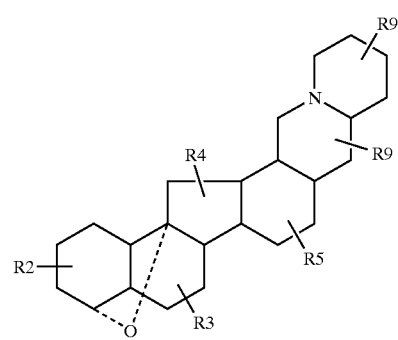

wherein $R_2$, $R_3$, $R_4$, $R_5$ and $R_9$ are as defined above;

In certain embodiments, the steroidal alkaloid is represented in the general formula (VII) or unsaturated forms thereof and/or seco-, nor- or homo-derivatives thereof:

Formula VII

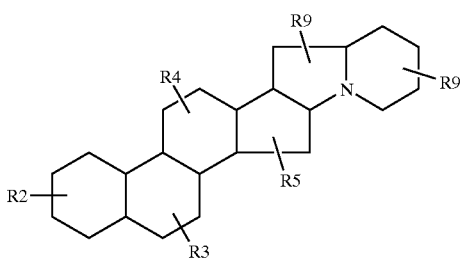

wherein $R_2$, $R_3$, $R_4$, $R_5$ and $R_9$ are as defined above.

In certain embodiments, the steroidal alkaloid does not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β,-methasone, prednisone, pregnane, pregnenolone, progesterone, spironolactone, testosterone, triamcinolone and their derivatives.

In certain embodiments, the steroidal alkaloid does not specifically bind a nuclear hormone receptor.

In certain embodiments, the steroidal alkaloid does not specifically bind estrogen or testerone receptors.

In certain embodiments, the steroidal alkaloid has no estrogenic activity at therapeutic concentrations.

In certain embodiments, the ptc agonist inhibits ptc loss-of-function or smoothened gain-of-function mediated signal transduction with an $ED_{50}$ of 1 mM or less.

In certain embodiments, the ptc agonist inhibits ptc loss-of-function or smoothened gain-of-function mediated signal transduction with an $ED_{50}$ of 1 $\mu$M or less.

In certain embodiments, the ptc agonist inhibits ptc loss-of-function or smoothened gain-of-function mediated signal transduction with an $ED_{50}$ of 1 nM or less.

In certain embodiments, the cell is contacted with the ptc agonist in vitro.

In certain embodiments, the cell is contacted with the ptc agonist in vivo.

In certain embodiments, the ptc agonist is administered as part of a therapeutic or cosmetic application.

In certain embodiments, the therapeutic or cosmetic application is selected from the group consisting of regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc.

In another aspect, the invention relates to a pharmaceutical preparation comprising a steroidal alkaloid represented in the general formulas (I), or unsaturated forms thereof and/or seco-, nor- or homo-derivatives thereof:

Formula I

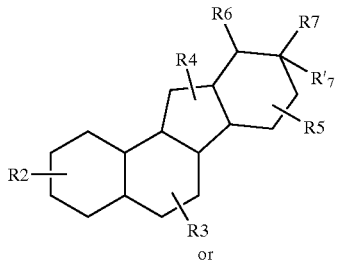

or

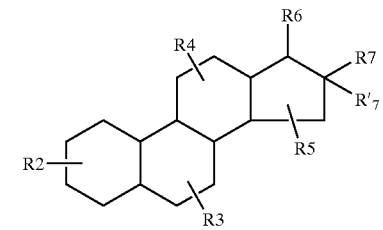

wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle; and m is an integer in the range 0 to 8 inclusive.

In another aspect, the invention provides a method for inhibiting an altered growth state of a cell having a ptc loss-of-function phenotype, hedgehog gain-of-function phenotype, or a smoothened gain-of-function phenotype, by contacting the cell with a composition including a cAMP agonist.

In certain embodiments, a cAMP agonist activates adenylate cyclase.

In certain embodiments, a cAMP agonist is a cAMP analog.

In certain embodiments, a cAMP agonist is a cAMP phosphodiesterase inhibitor.

In certain embodiments, the composition may include more than one cAMP agonist.

In certain embodiments, the composition inhibits ptc loss-of-function, hedgehog gain-of-function, or smoothened gain-of-function mediated signal transduction with an $ED_{50}$ of 1 mM or less.

In certain embodiments, the composition inhibits ptc loss-of-function, hedgehog gain-of-function, or smoothened gain-of-function mediated signal transduction with an $ED_{50}$ of 1 μM or less.

In certain embodiments, the composition inhibits ptc loss-of-function, hedgehog gain-of-function, or smoothened gain-of-function mediated signal transduction with an $ED_{50}$ of 1 nM or less.

In certain embodiments, the cell is contacted with the composition in vitro.

In certain embodiments, the cell is contacted with the composition in vivo.

In certain embodiments, the composition is administered as part of a therapeutic or cosmetic application.

In certain embodiments, the therapeutic or cosmetic application is selected from the group consisting of regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc.

In certain embodiments, the composition includes forskolin or a derivative thereof.

In yet another aspect, the invention relates to a method for treating or preventing basal cell carcinoma, comprising administering a composition including a cAMP agonist to a patient in an amount sufficient to inhibit progression of basal cell carcinoma.

In still another aspect, the invention relates to a method for inhibiting an altered growth state of a cell having a ptc loss-of-function phenotype, hedgehog gain-of-function phenotype, or a smoothened gain-of-function phenotype, by determining the phenotype of the cell; and, if the phenotype is a ptc loss-of-function, hedgehog gain-of-function, or a smoothened gain-of-function phenotype, treating the cell with a cAMP agonist in an amount sufficient to inhibit the altered growth state of the cell.

DETAILED DESCRIPTION OF THE INVENTION

I. Overview

Figure 1:
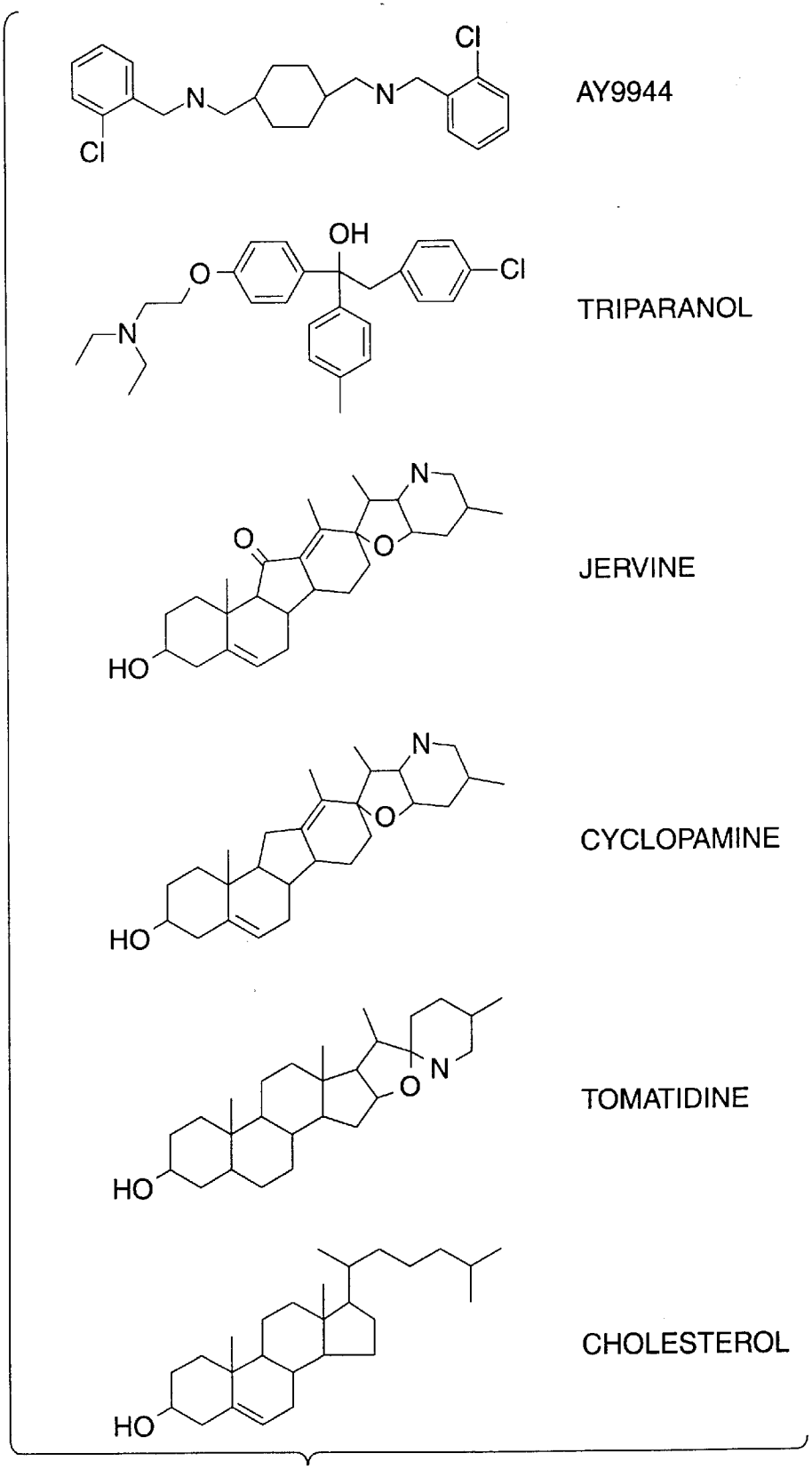
FIG. 1 presents structures of the synthetic compounds AY 9944 and triparanol, of the plant steriodal alkaloids jervine, cyclopamine and tomatidine, and of cholesterol.
Figure 2:
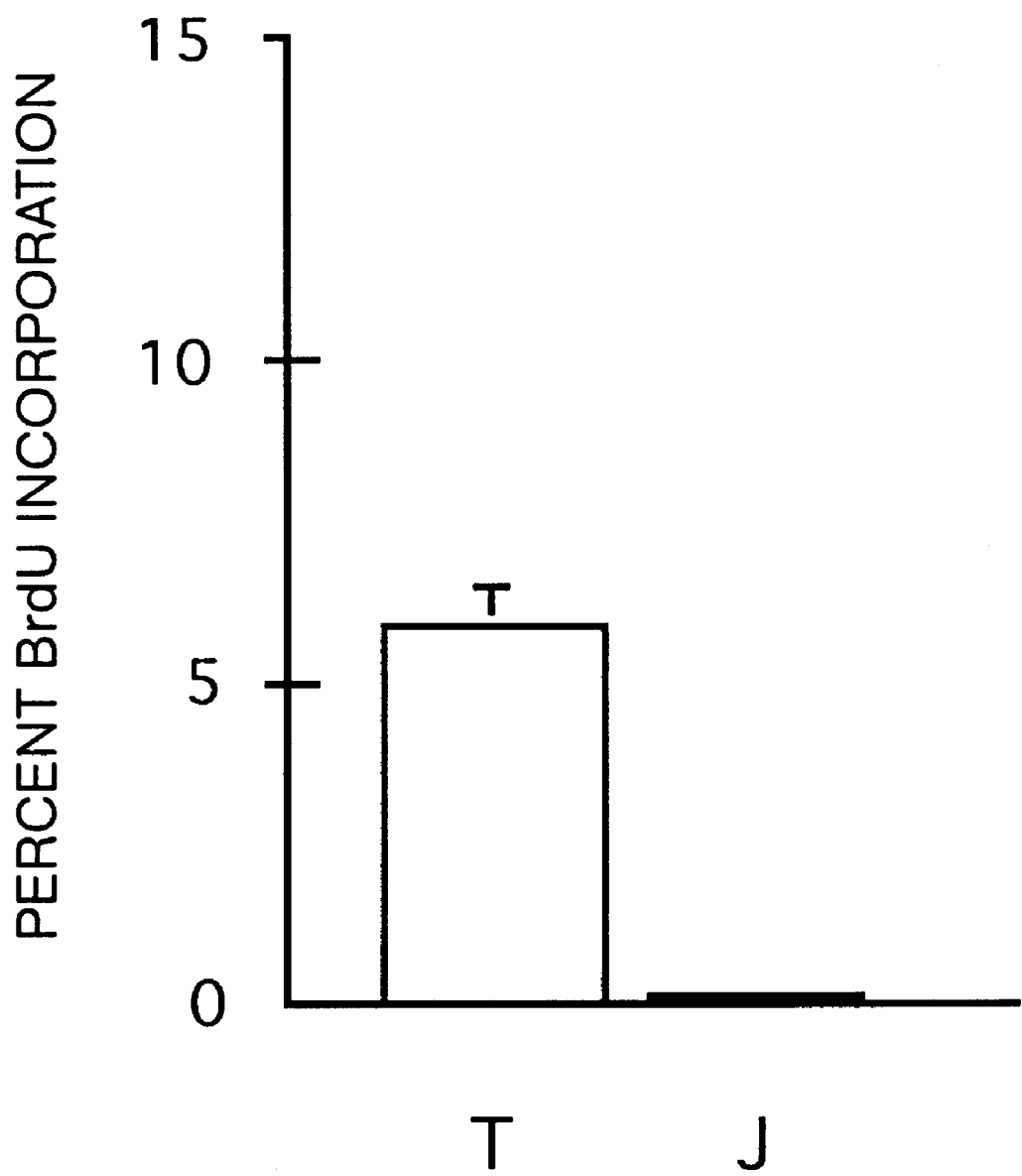
FIG. 2 shows inhibition of medulloblastoma cell proliferation by jervine.
Figure 3:
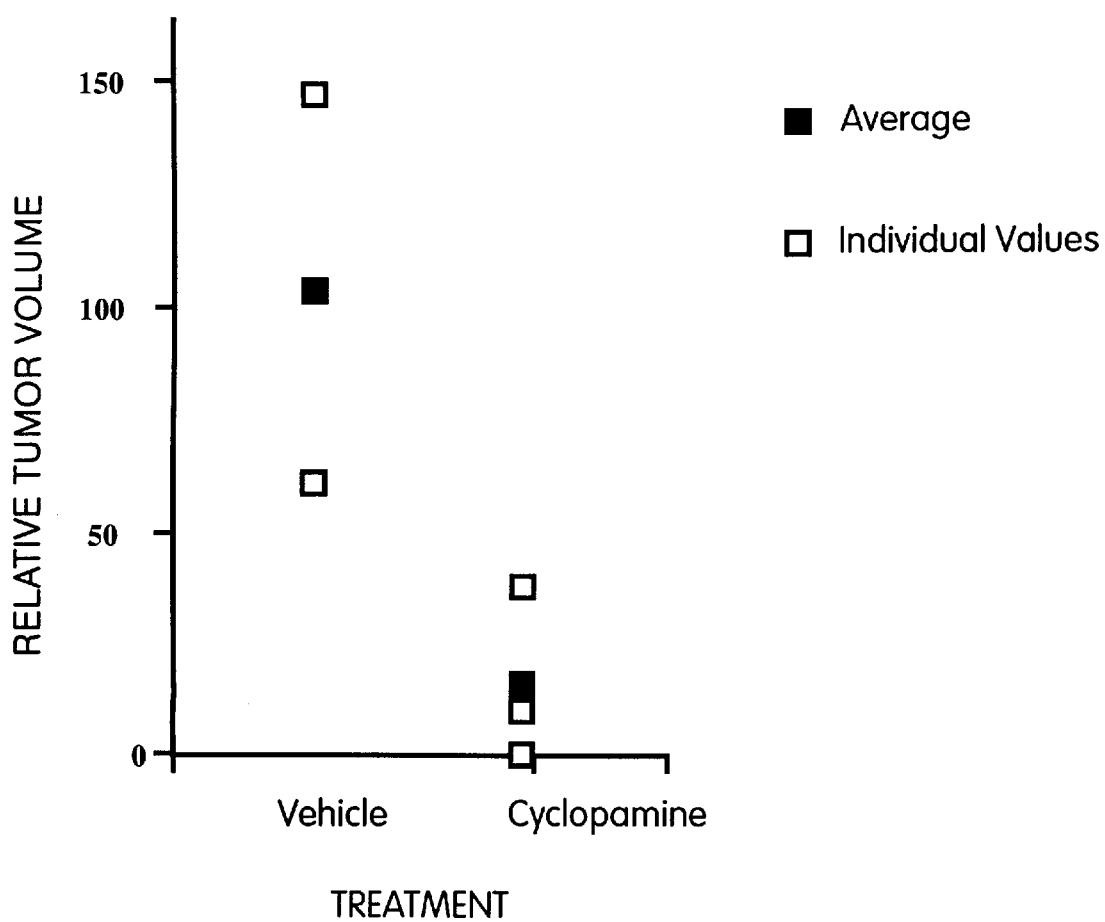
FIG. 3 illustrates the effect of cyclopamine treatment on medulloblastoma growth in vivo.

The present invention relates to the discovery that signal transduction pathways regulated by patched (ptc) and/or smoothened can be inhibited, at least in part, by steroidal alkaloids, and analogs thereof. As set out in more detail below, we have observed that members of the steroidal alkaloid class of compounds, such as the Veratrum-derived compound jervine, can inhibit proliferation of tumor cells with a loss-of-function mutation to patched ($ptc^{lof}$).

While not wishing to bound by any particular theory, the activation of a steroid hormone receptor may be the mechanism by which jermine acts. For example, the ability of jervine and other steroidal alkaloids to inhibit proliferation of the $ptc^{lof}$ cells may be due to the ability of such molecules to interact with patched or smoothened, or at least to interfere with the ability of those proteins to activate a ptc and/or smoothened-mediated signal transduction pathway.

It is, therefore, specifically contemplated that other small molecules, steroidal and non-steroidal in structure, which similarly interfere with aspects of ptc or smoothened signal transduction activity will likewise be capable of inhibiting proliferation (or other biological consequences) in cells having a patched loss-of-function phenotype or a smoothened gain-of-function phenotype. In preferred embodiments, the subject inhibitors are organic molecules having a molecular weight less than 2500 amu, more preferably less than 1500 amu, and even more preferably less than 750 amu, and are capable of inhibiting at least some of the biological activities of hedgehog proteins.

The present invention also relates to the discovery that signal transduction pathways regulated by hedgehog, patched (ptc), and/or smoothened can be regulated, at least in part, by agents, preferably small molecules, which regulate cAMP levels. While not wishing to bound by any particular theory, the activation of a receptor may be the mechanism by which these agents act. For example, the ability of these agents to inhibit proliferation of a patched loss-of-function (ptc$^{lof}$) cells may be due to the ability of such molecules to interact with hedgehog, patched, or smoothened, or at least to interfere with the ability of those proteins to activate a hedgehog, ptc, and/or smoothened-mediated signal transduction pathway.

It is, therefore, specifically contemplated that these agents, preferably small molecules, which increase or decrease effective cAMP levels and thus affect aspects of hedgehog, ptc, smoothened, or gli signal transduction activity will likewise be capable of inhibiting proliferation (or other biological consequences) in cells having a patched loss-of-function phenotype, a hedgehog gain-of-function phenotype, or a smoothened gain-of-function phenotype, or promote proliferation (or other biological consequences) in cells having a patched gain-of-function phenotype, a hedgehog loss-of-function phenotype, or a smoothened loss-of-function phenotype. In preferred embodiments, the subject cAMP regulators are organic molecules having a molecular weight less than 2500 amu, more preferably less than 1500 amu, and even more preferably less than 750 amu, and are capable of regulating at least some of the biological activities of hedgehog proteins, e.g., Hh, Shh, Ihh, and Dhh, preferably specifically in target cells.

Thus, the methods of the present invention include the use of agents, such as small molecules, which antagonize activity of the hedgehog pathway, including by lowering cAMP levels, resulting in the regulation of repair and/or functional performance of a wide range of cells, tissues, and organs having the phenotype of ptc loss-of-function, hedgehog gain-of-function, or smoothened gain-of-function. In an alternative embodiment, the present invention provides agents, such as small molecules, which agonize activity of the hedgehog pathway, resulting in the regulation of repair and/or functional performance of a wide range of cells, tissues, and organs having the phenotype of ptc gain-of-function, hedgehog loss-of-function, or smoothened loss-of-function. For instance, the subject methods have therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In a preferred embodiment, the subject method can be to treat epithelial cells having a phenotype of ptc loss-of-function, hedgehog gain-of-function, or smoothened gain-of-function employing an agent which antagonizes hedgehog function, e.g., by agonizing cAMP activity. For instance, the subject method can be used in treating or preventing basal cell carcinoma or other hedgehog pathway-related disorders. In an alternative embodiment, the subject method can be to treat epithelial cells having a phenotype of ptc gain-of-function, hedgehog loss-of-function, or smoothened loss-of-function employing an agent which agonizes hedgehog function, e.g., by antagonizing cAMP activity.

In another preferred embodiment, the subject method can be used as part of a treatment regimen for malignant medulloblastoma and other primary CNS malignant neuroectodermal tumors. As described in the appended examples, the subject method was effective both in vitro and in vivo at inhibiting proliferation of ptc$^{lof}$ medulloblastoma cells.

In another aspect, the present invention provides pharmaceutical preparations comprising, as an active ingredient, a hedgehog regulator such as described herein, formulated in an amount sufficient to regulate, in vivo, the hedgehog pathway, e.g., proliferation or other biological consequences of misexpression of, for example, ptc, hedgehog or smoothened. Additionally, the present invention provides pharmaceutical preparations comprising, as an active ingredient, a cAMP regulator such as described herein, formulated in an amount sufficient to regulate, in vivo, the hedgehog pathway, e.g., proliferation or other biological consequences of misexpression of ptc, hedgehog, or smoothened.

The subject treatments using the subject compounds can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Burn wounds" refer to cases where large surface areas of skin have been removed or lost from an individual due to heat and/or chemical agents.

The term "cAMP regulator" refers to an agent which alters the level or activity of cAMP in a cell, including agents which act upon adenylate cyclase, cAMP phosphodiesterase, or other molecules which, in turn, regulate cAMP levels or activity. Additionally, cAMP regulators, as the term is used herein, refer to downstream effectors of cAMP activity, such as protein kinase A. "cAMP agonists" refers to that subset of cAMP regulators which increases the level or activity of cAMP in a cell, while "cAMP antagonists" refers to the subset which decreases the level or activity of cAMP in a cell.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

An "effective amount" of, e.g., a cAMP regulator, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07–1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "hedgehog antagonist" refers to an agent which potentiates or recapitulates the bioactivity of patched, such as to repress transcription of target genes. Preferred hedgehog antagonists can be used to overcome a ptc loss-of-function and/or a smoothened gain-of-function, the latter also being refered to as smoothened antagonists. The term 'hedgehog antagonist' as used herein refers not only to any agent that may act by directly inhibiting the normal function of the hedgehog protein, but also to any agent that inhibits the hedgehog signalling pathway, and thus recapitulates the function of ptc. The term "hedgehog agonist" likewise refers to an agent which antagonizes or blocks the bioactivity of patched, such as to increase transcription of target genes. Preferred hedgehog antagonists can be used to overcome a ptc gain-of-function and/or a smoothened loss-of-function, the latter also being refered to as smoothened agonists.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signalling pathway would have a 'hedgehog gain-of-function' phenotype, even if hedgehog is not mutated in that cell. 'Hedgehog loss-of-function' refers to the direct opposite of a hedgehog loss-of-function, e.g., an aberrant modification or mutation that results in a phenotype which resembles contacting a cell with an agent which blocks hedgehog function.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "nail" refers to the horny cutaneous plate on the dorsal surface of the distal end of a finger or toe.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2 and Gli3.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "smoothened gain-of-function" refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) *Nature* 384: 177–179). The gene smo is a segment-polarity gene required for the correct patterning of every segment in Drosophila (Alcedo et al., (1996) *Cell* 86: 221–232). Human homologs of smo have been identified. See, for example, Stone et al. (1996) *Nature* 384:129–134, and GenBank accession U84401. The smoothened gene encodes an integral membrane protein with characteristics of heterotrimeric G-protein-coupled receptors; i.e., 7-transmembrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) *Nature* 384: 119–120). Rather, the binding of Sonic hedgehog (SHH) to its receptor, PTCH, is thought to prevent normal inhibition by PTCH of smoothened (SMO), a seven-span transmembrane protein.

Recently, it has been reported that activating smoothened mutations occur in sporadic basal cell carcinoma, Xie et al. (1998) Nature 391: 90–2, and primitive neuroectodermal tumors of the central nervous system, Reifenberger et al. (1998) *Cancer Res* 58: 1798–803.

The term "therapeutic index" refers to the therapeutic index of a drug defined as $LD_{50}/ED_{50}$.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "acylamino" is art-recognized and refers to a moiety that can be represented by the general formula:

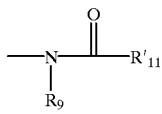

wherein $R_9$ is as defined above, and $R'_{11}$ represents a hydrogen, an alkyl, an alkenyl or $-(CH_2)_m-R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

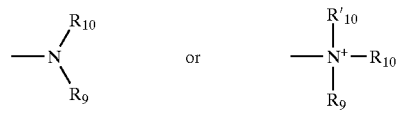

wherein $R_9$, $R_{10}$ and $R'_{10}$ each independently represent a hydrogen, an alkyl, an alkenyl, $-(CH_2)_m-R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or $-(CH_2)_m-R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

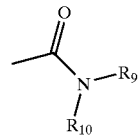

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

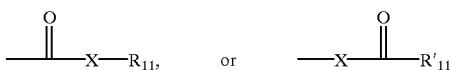

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

A "phosphonamidite" can be represented in the general formula:

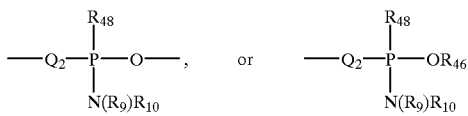

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in the general formula:

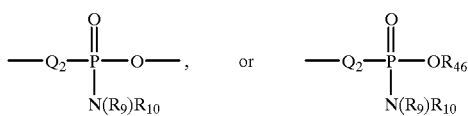

wherein $R_9$ and $R_{10}$ are as defined above, and $Q_2$ represents O, S or N.

A "phosphoryl" can in general be represented by the formula:

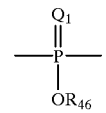

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

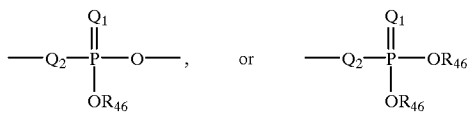

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2nd ed.*; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

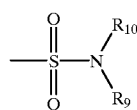

in which $R_9$ and $R_{10}$ are as defined above.

The term "sulfate" is art recognized and includes a moiety that can be represented by the general formula:

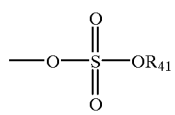

in which $R_{41}$ is as defined above.

The term "sulfonamido" is art recognized and includes a moiety that can be represented by the general formula:

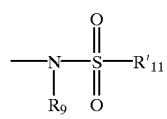

in which $R_9$ and $R'_{11}$ are as defined above.

The term "sulfonate" is art-recognized and includes a moiety that can be represented by the general formula:

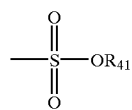

in which $R_{41}$ is an electron pair, hydrogen, alkyl, cycloalkyl, or aryl.

The terms "sulfoxido" or "sulfinyl", as used herein, refers to a moiety that can be represented by the general formula:

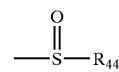

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Compounds of the Invention

As described in further detail below, it is contemplated that the subject methods can be carried out using a variety of different steroidal alkaloids, as well as non-steroidal small molecules, which can be readily identified, e.g., by such drug screening assays as described herein. The above notwithstanding, in a preferred embodiment, the methods and compositions of the present invention make use of compounds having a steroidal alkaloid ring system. Steroidal alkaloids have a fairly complex nitrogen containing nucleus. Two exemplary classes of steroidal alkaloids for use in the subject methods are the Solanum type and the Veratrum type.

There are more than 50 naturally occuring veratrum alkaloids including veratramine, cyclopamine, cycloposine, jervine, and muldamine occurring in plants of the Veratrum spp. The Zigadenus spp., death camas, also produces several veratrum-type of steroidal alkaloids including zygacine. In general, many of the veratrum alkaloids (e.g., jervine, cyclopamine and cycloposine) consist of a modified steroid skeleton attached spiro to a furanopiperidine. A typical veratrum-type alkaloid may be represented by:

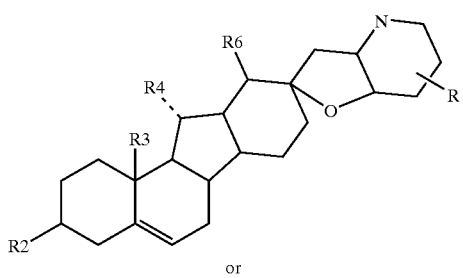

or

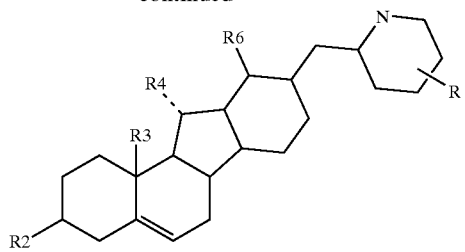

An example of the Solanum type is solanidine. This steroidal alkaloid is the nucleus (i.e. aglycone) for two important glycoalkaloids, solanine and chaconine, found in potatoes. Other plants in the Solanum family including various nightshades, Jerusalem cherries, and tomatoes also contain solanum-type glycoalkaloids. Glycoalkaloids are glycosides of alkaloids. A typical solanum-type alkaloid may be represented by:

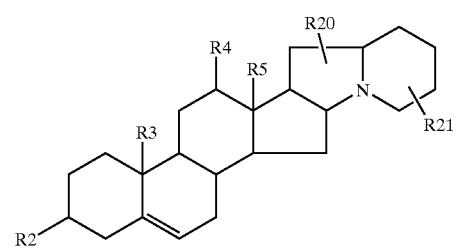

Based on these structures, and the possibility that certain unwanted side effects can be reduced by some manipulation of the structure, a wide range of steroidal alkaloids are contemplated as potential ptc agonists for use in the subject method. For example, compounds useful in the subject methods include steroidal alkaloids represented in the general formulas (I) or unsaturated forms thereof and/or seco-, nor- or homo-derivatives thereof:

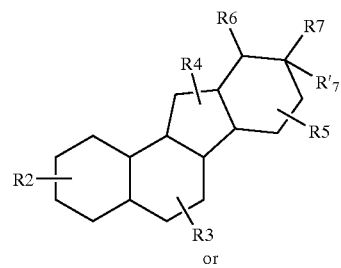

Formula I or

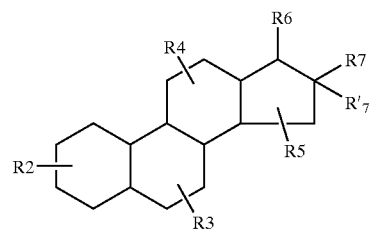

wherein, as valence and stability permit, $R_2$, $R_3$, $R_4$, and $R_5$, represent one or more substitutions to the ring to which each is attached, for each occurrence, independently represent hydrogen, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

$R_6$, $R_7$, and $R'_7$, are absent or represent, independently, halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$, or $R_6$ and $R_7$, or $R_7$ and $R'_7$, taken together form a ring or polycyclic ring, e.g., which is substituted or unsubstituted, with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle; and m is an integer in the range 0 to 8 inclusive.

In preferred embodiments, $R_2$ and $R_3$, for each occurrence, is an —OH, alkyl, —O-alkyl, —C(O)-alkyl, or —C(O)—$R_8$;

$R_4$, for each occurrence, is an absent, or represents —OH, =O, alkyl, —O-alkyl, —C(O)-alkyl, or —C(O)—$R_8$;

$R_6$, $R_7$, and $R'_7$ each independently represent, hydrogen, alkyls, alkenyls, alkynyls, amines, imines, amides, carbonyls, carboxyls, carboxamides, ethers, thioethers, esters, or —$(CH_2)_m$—$R_8$, or $R_7$, and $R'_7$ taken together form a furanopiperidine, such as perhydrofuro[3,2-b]pyridine, a pyranopiperidine, a quinoline, an indole, a pyranopyrrole, a naphthyridine, a thiofuranopiperidine, or a thiopyranopiperidine with the proviso that at least one of $R_6$, $R_7$, or $R'_7$ is present and includes a primary or secondary amine;

$R_8$ represents an aryl, a cycloalkyl, a cycloalkenyl, a heterocycle, or a polycycle, and preferably $R_8$ is a piperidine, pyrimidine, morpholine, thiomorpholine, pyridazine, In certain preferred embodiments, the definitions outlined above apply, and the subject compounds are represented by general formula Ia or unsaturated forms thereof and/or seco-, nor- or homo-derivatives thereof:

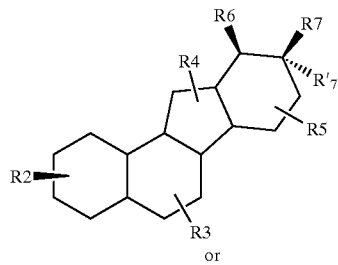

Formula Ia or

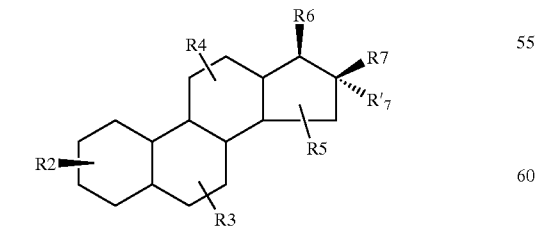

In preferred embodiments, the subject ptc agonists can be represented in one of the following general formulas (I) or unsaturated forms thereof and/or seco-, nor- or homo-derivatives thereof:

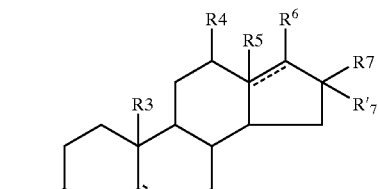

Formula II or

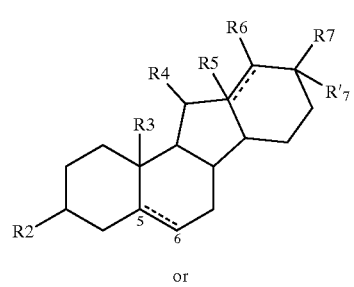

or

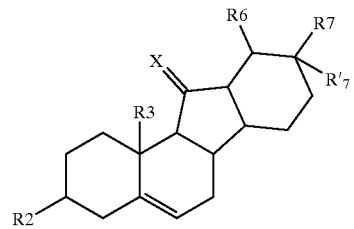

wherein $R_2$, $R_3$, $R_4$, $R_5$, $R_6$, $R_7$, and $R'_7$, are as defined above, and X represents O or S, though preferably O.

In certain preferred embodiments, the definitions outlined above apply, and the subject compounds are represented by general formula IIa or unsaturated forms thereof and/or seco- nor- of homo-derivatives thereof:

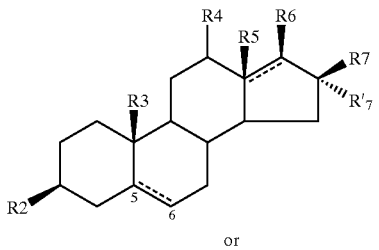

Formula IIa or

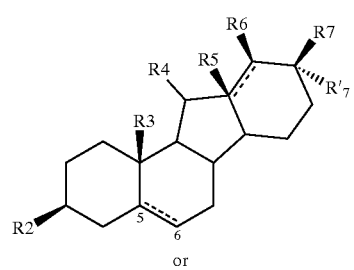

or

-continued

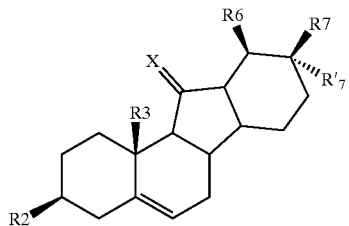

In certain embodiments, the subject ptc agonists are represented by the general formula (III) or unsaturated forms thereof and/or seco-, nor- or homo-derivatives thereof:

Formula III

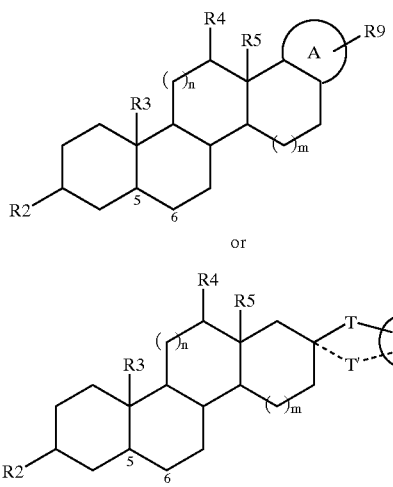

or wherein $R_2$, $R_3$, $R_4$, $R_5$ and $R_8$ are as defined above;

A and B represent monocyclic or polycyclic groups;

T represent an alkyl, an aminoalkyl, a carboxyl, an ester, an amide, ether or amine linkage of 1–10 bond lengths;

T' is absent, or represents an alkyl, an aminoalkyl, a carboxyl, an ester, an amide, ether or amine linkage of 1–3 bond lengths, wherein if T and T' are present together, than T and T' taken together with the ring A or B form a covelently closed ring of 5–8 ring atoms;

$R_9$ represent one or more substitutions to the ring A or B, which for each occurrence, independently represent halogens, alkyls, alkenyls, alkynyls, aryls, hydroxyl, =O, =S, alkoxyl, silyloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, seleno ethers, ketones, aldehydes, esters, or —$(CH_2)_m$—$R_8$; and n and m are, independently, zero, 1 or 2;

with the proviso that A and $R_9$, or T, T' B and $R_9$, taken together include at least one primary or secondary amine.

In certain preferred embodiments, the definitions outlined above apply, and the subject compounds are represented by general formula IIIa or unsaturated forms thereof and/or seco-, nor- or homo-derivatives thereof:

Formula IIIa

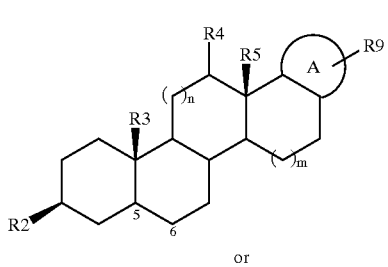

or

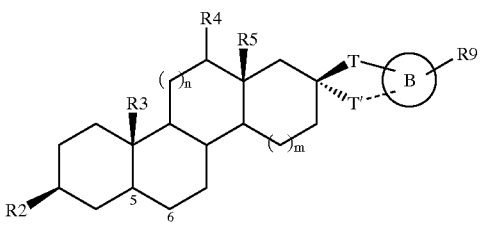

For example, the subject methods can utilize ptc agonists based on the veratrum-type steroidal alkaloids jervine, cyclopamine, cycloposine, mukiamine or veratramine, e.g., which may be represented in the general formula (IV) or unsaturated forms thereof and/or seco-, nor- or homo-derivatives thereof:

Formula IV

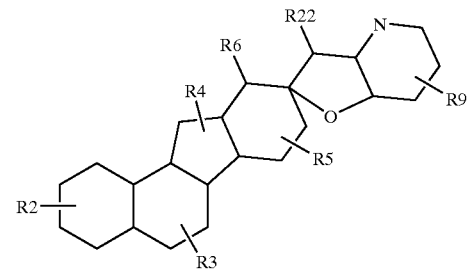

or

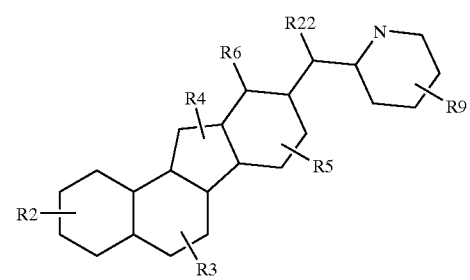

wherein $R_2$, $R_3$, $R_4$, $R_5$, $R_6$ and $R_9$ are as defined above;

$R_{22}$ is absent or represents an alkyl, an alkoxyl or —OH.

In certain preferred embodiments, the definitions outlined above apply, and the subject compounds are represented by general formula IVa or unsaturated forms thereof and/or seco-, nor- or homo-derivatives thereof:

Formula IVa

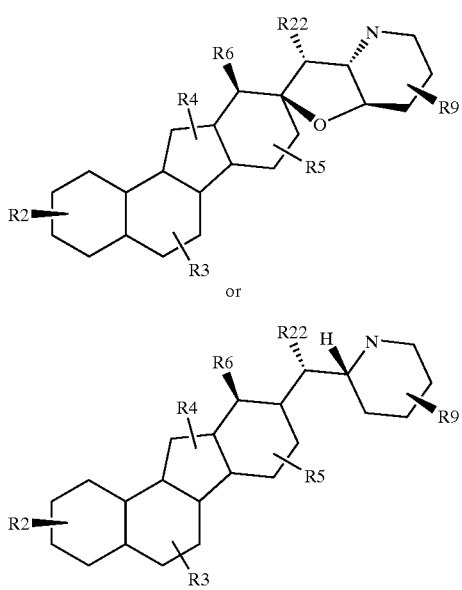

or

In even more preferred embodiments, the subject agonists are represented in the formulas (V) or unsaturated forms thereof and/or seco-, nor- or homo-derivatives thereof:

Formula V

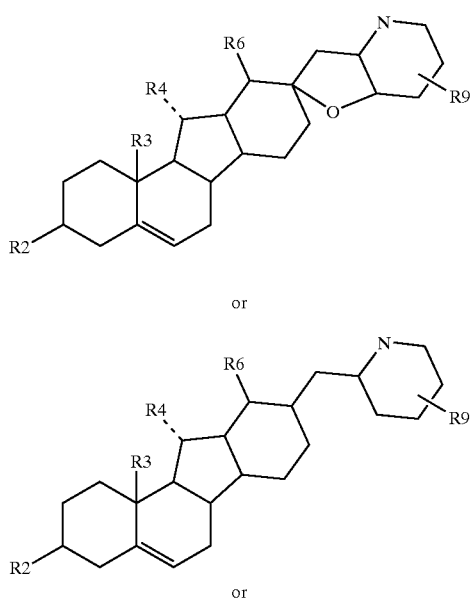

or

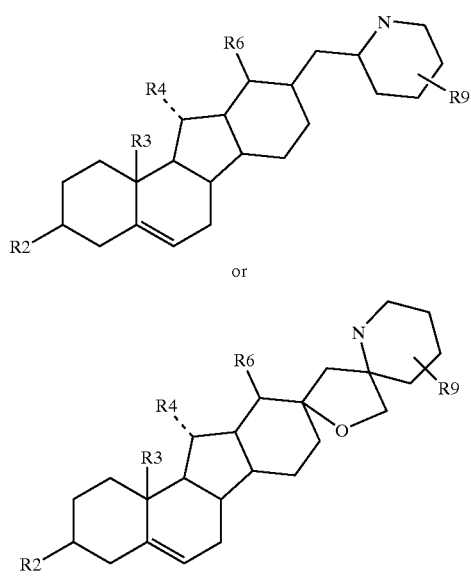

or wherein $R_2$, $R_3$, $R_4$, $R_6$ and $R_9$ are as define above;

In certain preferred embodiments, the definitions outlined above apply, and the subject compounds are represented by general formula Va or unsaturated forms thereof and/or seco-, nor- or homo-derivatives thereof:

Formula Va

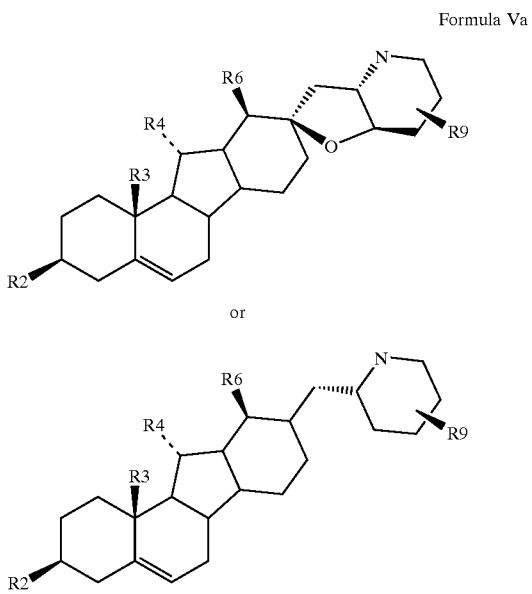

or

Another class of ptc agonists can be based on the veratrum-type steroidal alkaloids resembling verticine and zygacine, e.g., represented in the general formulas (VI) or unsaturated forms thereof and/or seco-, nor- or homo-derivatives thereof:

Formula VI

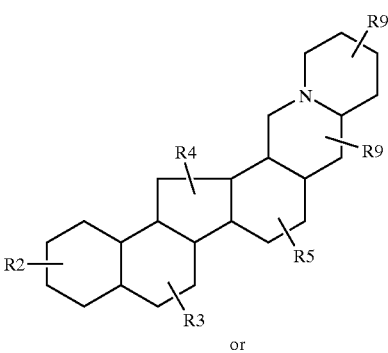

or

-continued

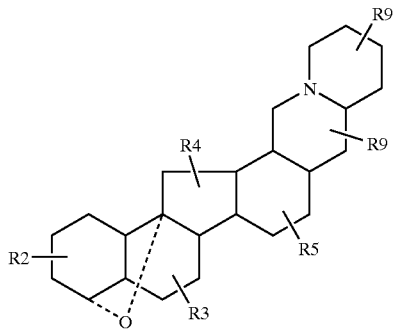

wherein $R_2$, $R_3$, $R_4$, $R_5$ and $R_9$ are as defined above.

In certain preferred embodiments, the definitions outlined above apply, and the subject compounds are represented by general formula VIa or unsaturated forms thereof and/or seco-, nor- or homo-derivatives thereof:

Formula VIa

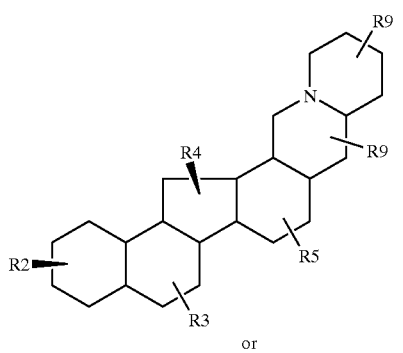

or

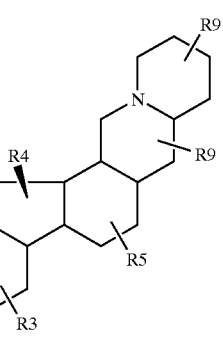

Still another class of potential ptc agonists are based on the solanum-type steroidal alkaloids, e.g., solanidine, which may be represented in the general formula (VII) or unsaturated forms thereof and/or seco-, nor- or homo-derivatives thereof:

Formula VII

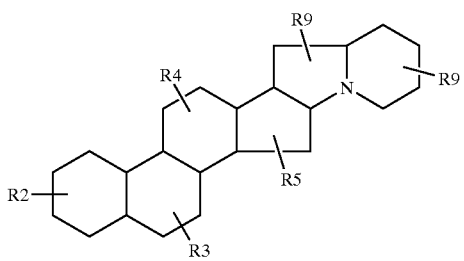

wherein $R_2$, $R_3$, $R_4$, $R_5$ and $R_9$ are as defined above.

In certain preferred embodiments, the definitions outlined above apply, and the subject compounds are represented by general formula VIIa or unsaturated forms thereof and/or seco-, nor- or homo-derivatives thereof:

Formula VIIa

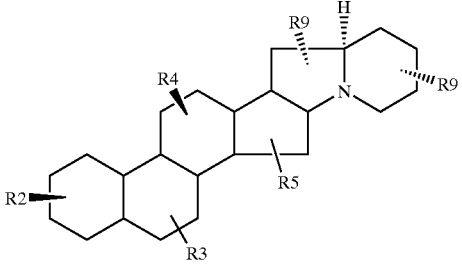

In certain embodiments, the subject agonists can be chosen on the basis of their selectively for the ptc/smoothened pathway(s). This selectivity can for the ptc/smoothened pathway(s) versus other steroid-mediated pathways (such as testosterone or estrogen mediated activities), as well as selectivity for particular ptc/smoothened pathways, e.g., which isotype specific for ptc (e.g., ptc-1, ptc-2). For instance, the subject method may employ steroidal alkaloids which do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-α, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc related signaling.

In one embodiment, the subject steroidal alkaloid for use in the present method has a $k_d$ for members of the nuclear hormone receptor superfamily of greater than 1 μM, and more preferably greater than 1 mM, e.g., it does not bind estrogen, testosterone receptors or the like. Preferably, the subject ptc agonist has no estrogenic activity at physiological concentrations (e.g., in the range of 1 ng–1 mg/kg).

In this manner, untoward side effects which may be associated certain members of the steroidal alkaloid class can be reduced. For example, using the drug screening assays described herein, the application of combinatorial and medicinal chemistry techniques to the steroidal alkaloids provides a means for reducing such unwanted negative side effects including personality changes, shortened life spans, cardiovascular diseases and vascular occlusion., organ toxicity, hyperglycemia and diabetes, Cushnoid features, "wasting" syndrome, steroidal glaucoma, hypertension, peptic ulcers, and increased susceptibility to infections. For certain embodiments, it will be beneficial to reduce the teratogenic activity relative to jervine, as for example, in the use of the subject method to selectively inhibit spermatogenesis.

In a preferred embodiment, the subject agonists are steroidal alkaloids other than spirosolane, tomatidine, jervine, etc.

In particular embodiments, the steroidal alkaloid is chosen for use because it is more selective for one patched isoform over the next, e.g., 10 fold, and more preferably at least 100 or even 1000 fold more selective for one patched pathway (ptc-1, ptc-2) over another.

As described in further detail below, it is contemplated that the subject methods which rely on modulation of cAMP levels can be carried out using a variety of different small molecules which can be readily identified, for example, by such drug screening assays as described herein. For example, compounds which may activate adenylate cyclase include forskolin (FK), cholera toxin (CT), pertussis toxin (PT), prostaglandins (e.g., PGE-1 and PGE-2), colforsin and β-adrenergic receptor agonists. β-Adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, norepinephrine, oxyfedrine, pirbuterol, prenalterol, procaterol, propranolol, protokylol, quinterenol, reproterol, rimiterol, ritodrine, salmefamol, soterenol, salmeterol, terbutaline, tretoquinol, tulobuterol, and xamoterol.

Compounds which may inhibit a cAMP phosphodiesterase include amrinone, milrinone, xanthine, methylxanthine, anagrelide, cilostamide, medorinone, indolidan, rolipram, 3-isobutyl-1-methylxanthine (IBMX), chelerythrine, cilostazol, glucocorticoids, griseolic acid, etazolate, caffeine, indomethacin, papverine, MDL 12330A, SQ 22536, GDPssS, clonidine, type III and type IV phosphodiesterase inhibitors, methylxanthines such as pentoxifylline, theophylline, theobromine, pyrrolidinones and phenyl cycloalkane and cycloalkene derivatives (described in PCT publications Nos. WO 92/19594 and WO 92/10190), lisophylline, and fenoxamine.

Analogs of cAMP which may be useful in the present method include dibutyryl-cAMP (db-cAMP), (8-(4)-chlorophenylthio)-cAMP (cpt-cAMP), 8-[(4-bromo-2,3-dioxobutyl)thio]-cAMP, 2-[(4-bromo-2,3-dioxobutyl)thio]-cAMP, 8-bromo-cAMP, dioctanoyl-cAMP, Sp-adenosine 3':5'-cyclic phosphorothioate, 8-piperidino-cAMP, $N^6$-phenyl-cAMP, 8-methylamino-cAMP, 8-(6-aminohexyl)amino-cAMP, 2'-deoxy-cAMP, $N^6$,2'-O-dibutryl-cAMP, $N^6$,2'-O-disuccinyl-cAMP, $N^6$-monobutyryl-cAMP, 2'-O-monobutyryl-cAMP, 2'-O-monobutryl-8-bromo-cAMP, $N^6$-monobutryl-2'-deoxy-cAMP, and 2'-O-monosuccinyl-cAMP.

Compounds which may reduce the levels or activity of cAMP include prostaglandylinositol cyclic phosphate (cyclic PIP), endothelins (ET)-1 and -3, norepinepurine, K252a, dideoxyadenosine, dynorphins, melatonin, pertussis toxin, staurosporine, $G_i$ agonists, MDL 12330A, SQ 22536, GDPssS and clonidine, beta-blockers, and ligands of G-protein coupled receptors. Additional compounds are disclosed in U.S. Pat. Nos. 5,891,875, 5,260,210, and 5,795,756.

Above-listed compounds useful in the subject methods may be modified to increase the bioavailability, activity, or other pharmacologically relevant property of the compound. For example, forskolin has the formula:

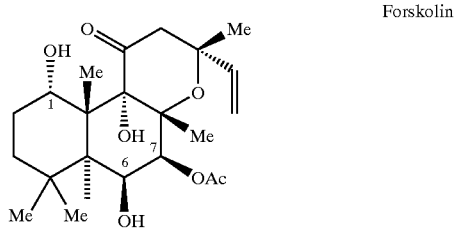

Forskolin

Modifications of forskolin which have been found to increase the hydrophilic character of forskolin without severely attenuating the desired biological activity include acylation of the hydroxyls at C6 and/or C7 (after removal of the acetyl group) with hydrophilic acyl groups. In compounds wherein C6 is acylated with a hydrophilic acyl group, C7 may optionally be deacetylated. Suitable hydrophilic acyl groups include groups having the structure —(CO)(CH$_2$)$_n$X, wherein X is OH or NR$_2$; R is hydrogen, a C$_1$–C$_4$ alkyl group, or two Rs taken together form a ring comprising 3–8 atoms, preferably 5–7 atoms, which may include heteroatoms (e.g., piperazine or morpholine rings); and n is an integer from 1–6, preferably from 1–4, even more preferably from 1–2. Other suitable hydrophilic acyl groups include hydrophilic amino acids or derivatives thereof, such as aspartic acid, glutamic acid, asparagine, glutamine, serine, threonine, tyrosine, etc., including amino acids having a heterocyclic side chain. Forskolin, or other compounds listed above, modified by other possible hydrophilic acyl side chains known to those of skill in the art may be readily synthesized and tested for activity in the present method.

Similarly, variants or derivatives of any of the above-listed compounds may be effective as cAMP agonists in the subject method. Those skilled in the art will readily be able to synthesize and test such derivatives for suitable activity.

In certain embodiments, the subject cAMP agonists can be chosen on the basis of their selectivity for cAMP activation.

In certain embodiments, it may be advantageous to administer two or more of the above cAMP agonists, preferably of different types. For example, use of an adenylate cyclase agonist in conjunction with a cAMP phosphodiesterase antagonist may have an advantageous or synergistic effect.

In certain preferred embodiments, the subject agents modulate hedgehog activity with an ED$_{50}$ Of 1 mM or less, more preferably of 1 μM or less, and even more preferably of 1 nM or less.

IV. Exemplary Applications of Method and Compositions

Another aspect of the present invention relates to a method of modulating a differentiated state, survival, and/or proliferation of a cell having a ptc loss-of-function, hedgehog gain-of-function, or smoothened gain-of-function, by contacting the cells with a compound as set forth above according to the subject method and as the circumstances may warrant. A related aspect of the present invention relates to a method of modulating a differentiated state, survival, and/or proliferation of a cell having a ptc gain-of-function, hedgehog loss-of-function, or smoothened loss-of-function, by contacting the cells with a cAMP antagonist according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The compound, whether inductive or anti-inductive with respect proliferation or differentiation of a given tissue, can be, as appropriate, any of the preparations described above.

For example, the present method of using subject compound is applicable to cell culture techniques wherein, whether for genetic or biochemical reasons, the cells have a ptc loss-of-function, hedgehog gain-of-function, or smoothened gain-of-function phenotype. Alternatively, a subject compound may be employed in a related method directed towards cells which have a ptc loss-of-function, hedgehog gain-of-function, or smoothened gain-of-function phenotype. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such sultures for the generation of new neurons and glia. In such embodiments of the subject method, the cultured cells can be contacted with a compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be effected by contact with compounds of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a subject compound.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6–8, more preferably close to pH 7, even more particularly about pH 7.4. Cells should be cultured at a temperature close to physiological temperature, preferably between 30° C.–40° C., more preferably between 32° C.–38° C., and most preferably between 35° C.–37° C.

Cells can be grown in suspension or on a fixed substrate, but proliferation of the progenitors is preferably done in suspension to generate large numbers of cells by formation of "neurospheres" (see, for example, Reynolds et al. (1992) Science 255:1070–1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3–4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3–10 days in vitro, the proliferating clusters (neurospheres) are fed every 2–7 days, and more particularly every 2–4 days by gentle centrifugation and resuspension in medium containing growth factor.

After 6–7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a subject compound.

To further illustrate other uses of the subject compounds, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of compounds employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The subject compounds can be used alone, or can be used in combination with other neurotrophic factors which act to more particularly enhance a particular differentiation fate of the neuronal progenitor cell.

In addition to the implantation of cells cultured in the presence of the subject compounds, yet another aspect of the present invention concerns the therapeutic application of a subject compound to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject compounds can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubulated by use of a prosthetic device, subject compounds can be added to the prosthetic device to regulate the rate of growth and regeneration of the dendridic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the subject compounds can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the subject compounds can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, compounds of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of subject compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising subject compounds can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) Curr Biol 7:801–4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject compounds can be used to control or regulate the proliferation and/or differentiation of pancreatic tissue both in vivo and in vitro.

There are a wide variety of pathological cell proliferative and differentiative conditions for which the inhibitors of the present invention may provide therapeutic benefits, with the general strategy being, for example, the correction of abberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and smoothened signaling may be indicated in disease progression, the subject regulators can be used to enhance regeneration of the tissue after antitumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonic traits in mature β-cells can be observed. By utilizing the subject compounds, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) *Biochem Biophys Res Commun* 238:658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., basal cell carcinoma, medulloblastoma, meningioma, etc.), tumors evidenced in pct knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising one or more of the subject compounds can be used in the in vitro generation of skeletal tissue, such as from skeletal stem cells, as well as the in vivo treatment of skeletal tissue deficiencies. The present invention particularly contemplates the use of subject compounds to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a subject compound to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject regulators may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a subject compound during certain stages of the culturing process in order to manage the rate of differentiation of chondrocytes and the formation of hypertrophic chondrocytes in the culture.

In another embodiment, the implanted device is treated with a subject compound in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a compound of the present invention can be employed as part of a method for regulating the rate of bone loss in a subject. For example, preparations comprising subject compounds can be employed, for example, to control endochondral ossification in the formation of a "model" for ossification.

In yet another embodiment of the present invention, a subject compound can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a preferred embodiment, the subject compound can be used as a contraceptive. In similar fashion, compounds of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a subject compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a subject compound can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of subject compounds can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a preparation of a subject compound into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The subject method can also provide a process for extending the duration of depilation.

Moreover, because a subject compound will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, subject compounds can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic preparation of a subject compound can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a subject compound, e.g., which promotes quiescense or differentiation, can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activiation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a subject compound composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum* ovale, a yeast. Treatment with an antiproliferative subject compound, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange.

In still another embodiment, the subject method can be used in the treatment of human cancers, particularly basal cell carcinomas and other tumors of epithelial tissues such as the skin. For example, subject compounds can be employed, in the subject method, as part of a treatment for basal cell nevus syndrome (BCNS), and other other human carcinomas, adenocarcinomas, sarcomas and the like.

In a preferred embodiment, the subject method is used as part of a treatment of prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) *Science* 277:1109–13; Xie et al. (1997) *Cancer Res* 57:2369–72; Oro et al. (1997) *Science* 276:817–21; Xie et al. (1997) *Genes Chromosomes Cancer* 18:305–9; Stone et al. (1996) *Nature* 384:129–34; and Johnson et al. (1996) *Science* 272:1668–71.

The subject method can also be used to treatment patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

It will be apparent to one of ordinary skill that certain instances described above may respond favorably to administration of a hedgehog agonist or antagonist, such as a cAMP agonist or antagonist, depending on the particular effect on the hedgehog pathway desired. For example, although a hedgehog agonist may be useful in maintaining a culture of undifferentiated stem cells, a hedgehog antagonist may be employed to maintain a differentiation state in a culture of differentiated cells. Such methods are considered to fall within the scope of the present invention.

In another aspect, the present invention provides pharmaceutical preparations comprising the subject compounds. The compounds for use in the subject method may be conveniently formulated for administration with a biologically acceptable and/or sterile medium, such as water, buffered saline, polyol (for example, glycerol, propylene glycol, liquid polyethylene glycol and the like) or suitable mixtures thereof. The optimum concentration of the active ingredient (s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the subject compounds, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the subject compounds suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The subject compounds according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "therapeutically effective amount" as used herein means that amount of a compound, material, or composition comprising a compound of the present invention which is effective for producing some desired therapeutic effect, e.g., by overcoming a ptc loss-of-function, hedgehog gain-of-function, or smoothened gain-of-function, in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$ cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the subject compounds in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" 0 and B books, Corvallis, Oreg., U.S.A., 1977).

VI. Synthetic Schemes and Identification of Active Regulators

The subject compounds, and derivatives thereof, can be prepared readily by employing known synthetic methodology. As is well known in the art, these coupling reactions are carried out under relatively mild conditions and tolerate a wide range of "spectator" functionality. Additional compounds may be synthesized and tested in a combinatorial fashion, to facilitate the identification of additional compounds which may be employed in the subject method.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog regulator lead compounds, as well as to refine the specificity, toxicity, and/or cytotoxic-kinetic profile of a lead compound. For instance, ptc, hedgehog, or smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened. Alternatively, bioactivity assays using cells with either a ptc gain-of-function, hedgehog loss-of-function, or smoothened loss-of-function, can be used to screen a library of the subject compounds for those having antagonist activity toward ptc or agonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject compounds can be synthesized and screened for particular activity or property.

In an exemplary embodiment, a library of candidate compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with, for example, ptc loss-of-function, hedgehog gain-of-function, or smoothened gain-of-function cells for which a hedgehog agonist is sought. The diversomers can be released from the bead, e.g. by hydrolysis.

Many variations on the above and related pathways permit the synthesis of widely diverse libraries of compounds which may be tested as regulators of hedgehog function.

b. Screening Assays

There are a variety of assays available for determining the ability of a compound such as a hedgehog regulator to regulate ptc, smoothened, or hedgehog function, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are hedgehog regulators.

In addition to cell-free assays, test compounds can also be tested in cell-based assays. In one embodiment, cell which have a ptc loss-of-function, hedgehog gain-of-function, or smoothened gain-of-function phenotype can be contacted with a test agent of interest, with the assay scoring for, e.g., inhibition of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are the patched gene (Hidalgo and Ingham, 1990 Development 110, 291–301; Marigo et al., 1996) and the vertebrate homologs of the drosophila cubitus interruptus gene, the GLI genes (Hui et al. (1994) Dev Biol 162:402–413). Patched gene expression has been shown to be induced in cells of the limb bud and the neural plate that are responsive to Shh. (Marigo et al. (1996) *PNAS* 93:9346–51; Marigo et al. (1996) *Development* 122:1225–1233). The Gli genes encode putative transcription factors having zinc finger DNA binding domains (Orenic et al. (1990) *Genes & Dev* 4:1053–1067; Kinzler et al. (1990) *Mol Cell Biol* 10:634–642). Transcription of the Gli gene has been reported to be upregulated in response to hedgehog in limb buds, while transcription of the Gli3 gene is downregulated in response to hedgehog induction Narigo et al. (1996) *Development* 122:1225–1233). By selecting transcriptional regulatory sequences from such target genes, e.g., from patched or Gli genes, that are responsible for the up- or down-regulation of these genes in response to hedgehog signalling, and operatively linking such promoters to a reporter gene, one can derive a transcription based assay which is sensitive to the ability of a specific test compound to modify hedgehog-mediated signalling pathways. Expression of the reporter gene, thus, provides a valuable screening tool for the development of compounds that act as regulators of hedgehog.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc loss-of-function, hedgehog gain-of-function, smoothened gain-of-function, or stimulation by SHH itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or antagonized the gain-of-function hedgehog or smoothened signal), e.g., the test compound is a potential hedgehog antagonist.

Exemplification

The invention now being generally described, it will be more readily understood by reference to the following examples which are included merely for purposes of illustration of certain aspects and embodiments of the present invention, and are not intended to limit the invention.

Steroidal Alkaloids

Effects in vitro

To determine the effects of jervine and cyclopamine on cell proliferation mediated by activation of the Hedgehog (Hh) signaling pathway, medulloblastoma tumor cells were grown in primary culture. These medulloblastoma cells were derived from tumors that arose in the brains of mice heterozygous for an inactivating mutation in the ptc gene ("heterozygous ptc knockout mice"). Mutation of ptc leads to inappropriate activation of the Hh signaling pathway, and in these ptc knockout mice, the ptc mutation results in the occurrence of medulloblastomas. The medulloblastoma tumor cells were placed into primary culture in neuronal culture medium (Basal Medium of Eagle, with 10% calf serum, 25 mM KCl, and 2 mM glutamine). Cells were typically seeded at 0.5 or $1.0 \times 10^6$ cells/well of a 24 well plate, in 0.5 ml of medium per well. One day after seeding (i.e., on 1 day in vitro, or DIV), the cells were treated with cyclopamine or jervine (10 $\mu$M final concentration), or an equal amount of a control compound (tomatidine, which is not known to inhibit the Hh signaling pathway), or vehicle (0.1% ethanol, final concentration). From 2–3 DIV, bromodeoxyuridine (BrdU) was added to the cultures, to label proliferating cells. On 3 DIV, cells were fixed with paraformaldehyde. Cells were then immunostained with an antibody to BrdU to identify cells that had been proliferating in culture, and counterstained with bisbenzimide (Hoechst 33258) to determine total cell number. The numbers of total and BrdU(+) cells were then scored in multiple fields in wells of each condition, to determine the percent proliferating cells under different treatments. The scorer was blinded as to the treatments of the cells. Both jervine and cyclopamine were found to strongly inhibit proliferation of the medulloblastoma cells. For example, in a typical experiment, the percent proliferation was 5.9% under control conditions (tomatidine), but only 0.2% with jervine treatment. This indicates that Hh pathway inhibitors can inhibit the proliferation of tumor cells that involve activation of the Hh signaling pathway.

Effects in vivo

To determine whether Hh signaling pathway inhibitors can inhibit tumor growth in vivo, medulloblastoma cells from ptc knockout mice were transplanted into the brains of athymic ("nude") mice. After allowing time for the tumor cells to grow at the injection site (e.g., 5 weeks), the transplanted mice were divided into two groups. In one group, mice were treated with once-daily intraperitoneal injections of cyclopamine at a dose of 1.1 mg/kg. The mice in the other group received an equivalent injection of vehicle (2.5% ethanol). Mice were treated for 14 days [one animal in the cyclopamine group became sick and was therefore processed on day 12]. Mice were then sacrificed and fixed by perfusion with a paraformaldehyde/glutaraldehyde mix, and brains were removed and sectioned on a vibratome. The transplanted medulloblastoma cells from the ptc knockout mice contain a lacZ transgene encoding β-galactosidase. Therefore, the brain sections were stained for β-galactosidase activity using the substrate Xgal, which stains expressing cells blue, to identify the tumor cells. The volume of the tumor was then determined by measuring the area of the (blue) tumor region on successive vibratome slices. The mice treated with cyclopamine were found to have smaller tumors than did the control mice. The average tumor size in the control mice was 104.2 (relative volume units, N=2 mice), while the cyclopamine-treated mice had an average tumor volume of only 16.0 (N=3 mice). This result suggests that systemic treatment with cyclopamine inhibited tumor growth in vivo. The cyclopamine-treated mice appeared healthy, which is consistent with the fact that the dose that appeared effective here (1.1 mg/kg) is much lower than the dose of jervine previously reported to cause toxicity. For example, Omnell et al. (Teratology 42: 105, 1990) report an LD50 for jervine of 120 to 260 mg/kg, depending on mouse strain, for jervine-induced death. These results suggest that tumors involving activation of the Hh signaling pathway may be effectively inhibited in vivo by treatment with cyclopamine, jervine, or other Hh signaling inhibitors.

cAMP Regulators

Effects in vitro

Figure 4:
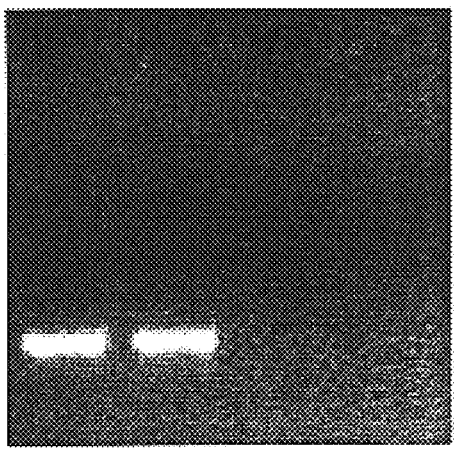
FIG. 4 depicts inhibition of gli-1 gene expression by forskolin treatment of medulloblastoma cells in vitro.
Figure 4:
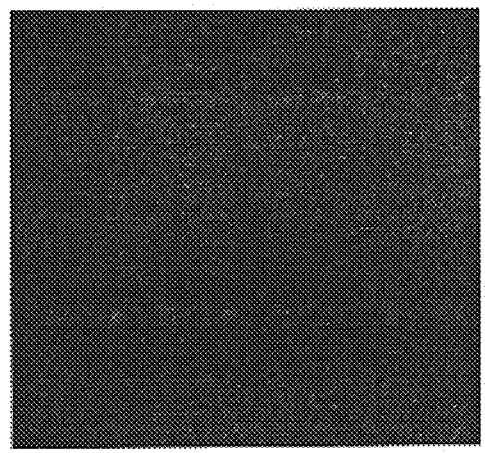

To determine the effects of cAMP agonist drugs on the Hedgehog (Hh) signaling pathway in tumor cells, medulloblastoma cells were grown in primary culture. These medulloblastoma brain tumors arose in mice heterozygous for an inactivating mutation in the ptc-1 gene ("heterozygous ptc knockout mice"). Mutation of ptc-1 leads to inappropriate activation of the Hh signaling pathway, and in these ptc-1 knockout mice, the ptc-1 mutation results in the occurrence of medulloblastoma. The medulloblastoma tumor cells were placed into primary culture in neuronal culture medium (Basal Medium of Eagle, with 10% serum, 25 mM KCl, and 2 mM glutamine). Cells were typically seeded at 0.5 or 1.0×10 cells/well of a 24 well plate, in 0.5 ml of medium. One day after seeding (i.e., on 1 day in vitro, or DIV), cells were treated with forskolin (50 $\mu$M final), or an equal amount of vehicle (0.1% DMSO). On 3 DIV, RNA was isolated from the cells, and the expression of the Hh-response gene gli-1 was determined by RT-PCR analysis. Forskolin was found to strongly inhibit gli-1 expression (FIG. 4), indicating that cAMP agonist drugs can inhibit the Hh pathway in such tumor cells.

Figure 5:
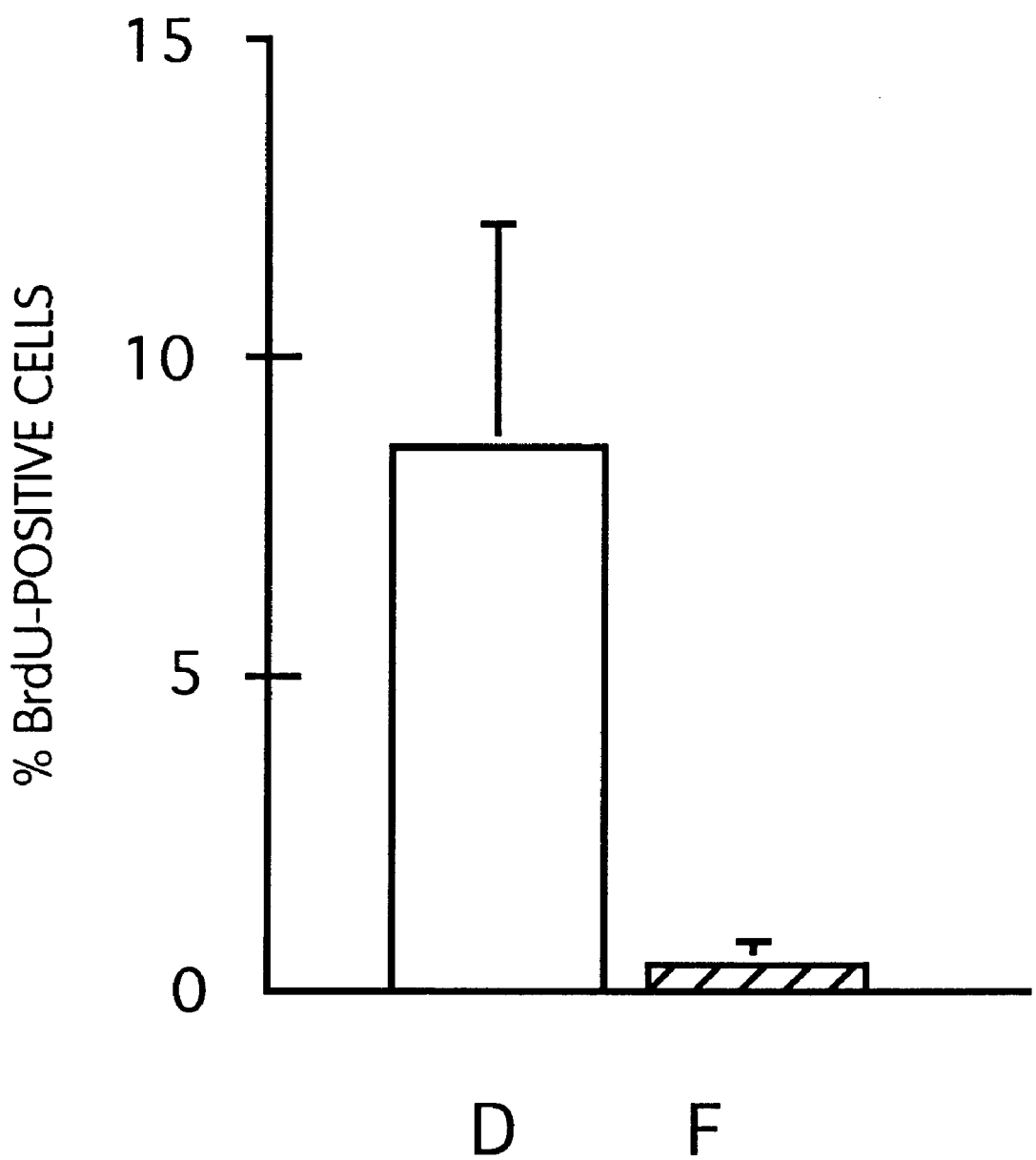
FIG. 5 presents inhibition of medulloblastoma cell proliferation by forskolin in vitro. D=DMSO, F=forskolin (50 μM); error bars represent value range of duplicate wells.
Figure 6:
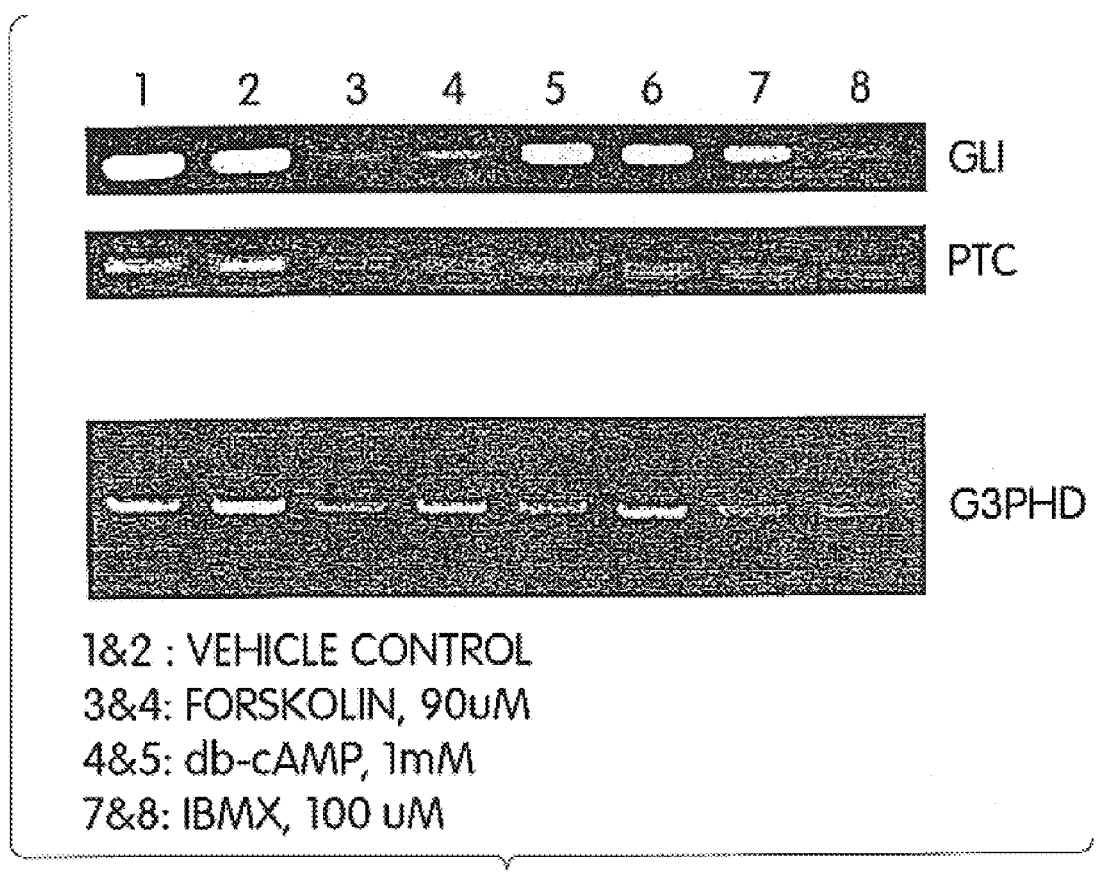
FIG. 6 demonstrates the effect of cAMP elevating agents on IH-22 cells.
Figure 7:
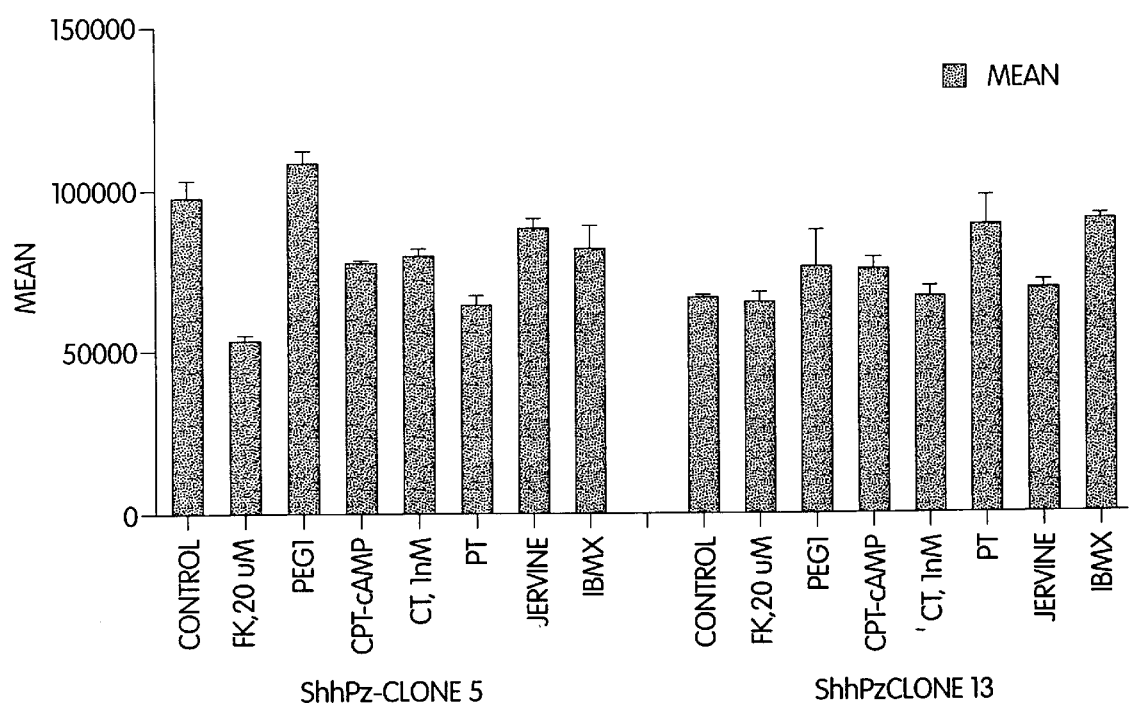
FIGS. 7 and 8 show the result of treating Pam212 keratinocytes with cAMP elevating agents.
Figure 8:
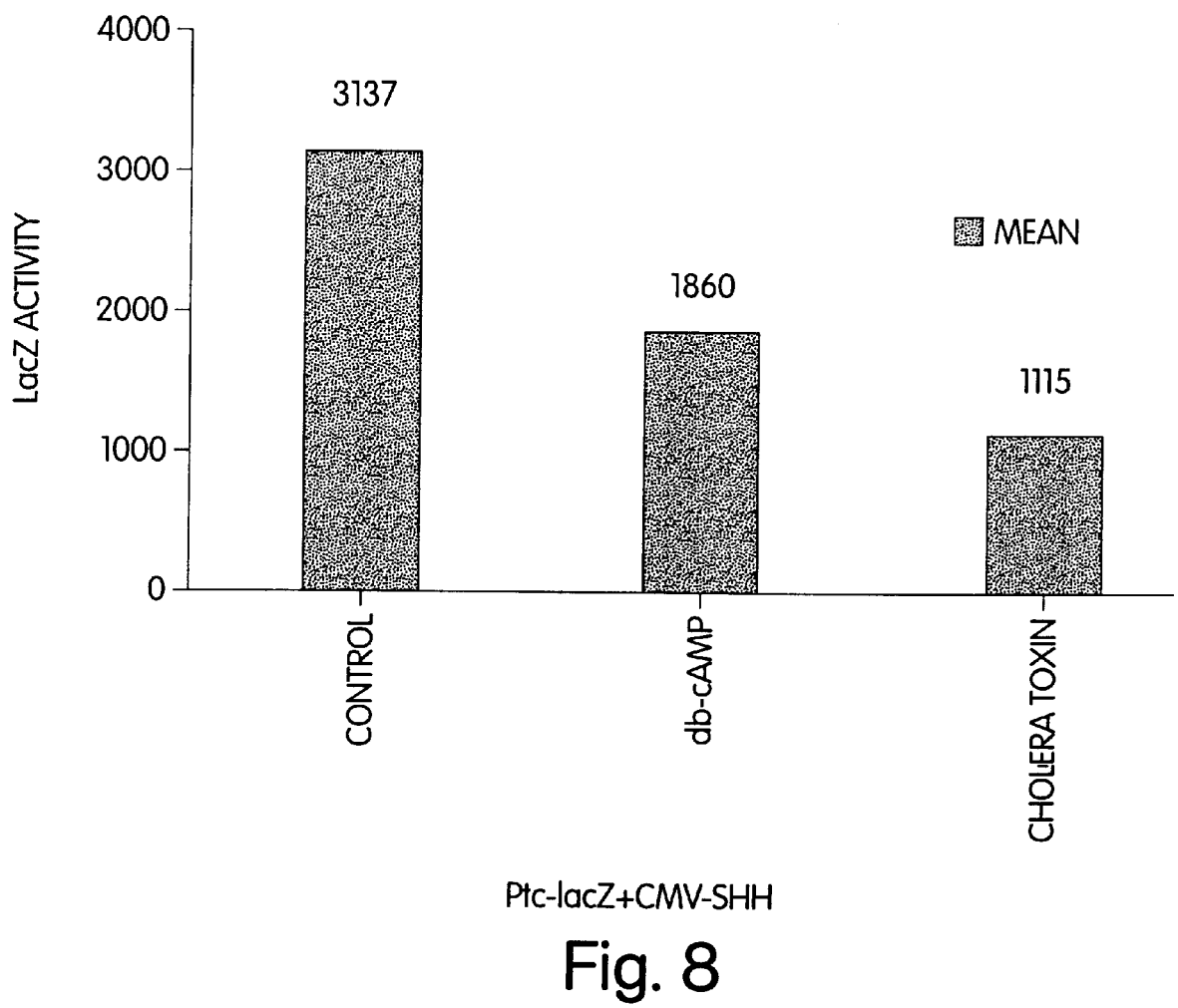
Figure 9:
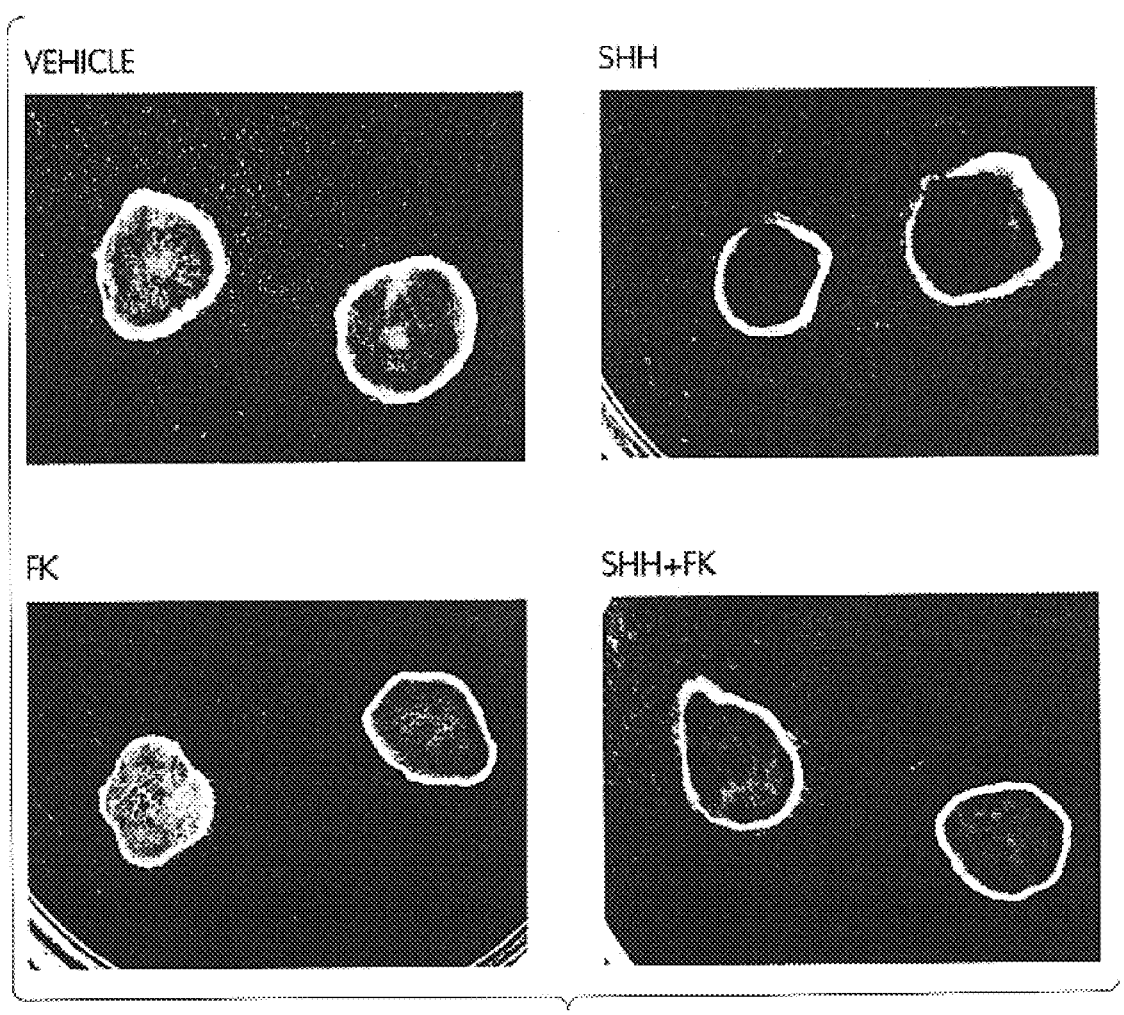
FIG. 9 depicts the effects of forskolin and Shh on skin samples.

In order to test the effects of cAMP agonists on the proliferation of Hh-pathway tumor cells, primary medulloblastoma cell cultures were similarly treated with forskolin or control vehicle. From 2–3 DIV, bromodeoxyuridine (BrdU) was then added to the cultures, to label proliferating cells. On 3 DIV, cells were fixed with paraformaldehyde. Cells were then immunostained with an antibody to BrdU to identify cells that had been proliferating, and counterstained with bisbenzimide to determine total cell number. The number of total and BrdU(+) cells were then scored in multiple fields in wells of each condition, to determine the percent proliferating cells under different treatments. The scorer was blinded as to the treatments of the cells. Forskolin was found to strongly inhibit proliferation of the medulloblastoma cells. For example, in a typical experiment (FIG. 5), the percent proliferation was 8.6% under control conditions (DMSO), but only 0.4% with forskolin treatment (=95% inhibition). Similar results were obtained when proliferation was measured using a tritiated thymidine incorporation assay, and other cAMP agents were also found to be effective. For example, in a typical assay, forskolin caused 93% inhibition of tritiated thymidine incorporation into the medulloblastoma cells; the forskolin analogue 7-deacetyl-7-[O-(N-methylpiperazino)-gamma-butyryl]-forskolin ("H-forskolin") caused 91% inhibition. Together, these results indicate that Hh pathway inhibitors can inhibit the proliferation of tumor cells that involve activation of the Hh signaling pathway.

cAMP agonists inhibit the expression of both ptc and gli 1 in the IH22 cell line, a mouse 10T1/2 fibroblast line transfected with an Indian Hedgehog cDNA expression plasmid and therefore having a constitutively activated Hh pathway. For these experiments, IH22 cells were grown in 10% DMEM in the presence of various cAMP elevating agents. Five days later, total RNA was isolated from the cells and used for RT-PCR. Specific primers for the detection of mouse ptc and gli expression were used in the PCR, and the G3PDH gene was used for normalizing the PCR efficiency. PCR products were then loaded on 1.5% agarose gel for detection. Results are presented in FIG. 6. Lanes 1 and 2 are control lanes (application of vehicle only), lanes 3 and 4 are forskolin (90 $\mu$M), lanes 5 and 6 are db-CAMP (1 mM), and lanes 7 and 8 are IBMX (100 $\mu$M).

cAMP agonists can inhibit the Hh pathway in a PAM212 mouse keratinocyte line that carries both CMV—SHH and Ptc-lacZ plasmids in a quantitative lacZ assay (FIG. 7). Similar results were obtained from a transient transfection of Pam212 cells with these two plasmids (FIG. 8). For these experiments, a Pam212 stable cell line Shh-Pz #5 was established after transfection of both CMV—SHH plasmid that expresses Shh and Ptc-lacZ plasmid that expresses lacZ gene from the ptc promoter. The constitutively expressed Shh can activate the expression of lacZ from the ptc promoter in this cell line. Shh-Pz#5 cells were grown in the presence of the cAMP elevating agents for 48 hrs. The cells were then lysed for the detection of lacZ activity. The Shh-Pz#13 clone, which exhibits Hh pathway-independent expression of lacZ, serves as a negative control. In transient transfection assay, Pam212 cells were transfected with both CMV-SHH and Ptc-lacZ plasmids. Twenty-four hours after transfection, the cAMP agonists were added to the cells and the cells were incubated for another 24 hours. The cells were then lysed for lacZ assay.

cAMP elevating agents decreased Ptc-lacZ activity in a skin sample assay, suggesting it inhibits Hh pathway. For these experiments, skin samples were taken from E17.5 Ptc-lacZ skin and cultured in an air-liquid interface for 6 days with Hh proteins and/or forskolin. The skin samples were then fixed for Xgal staining and processed for histology analysis. The results are presented in FIG. 9.

Effects in vivo

Figure 10:
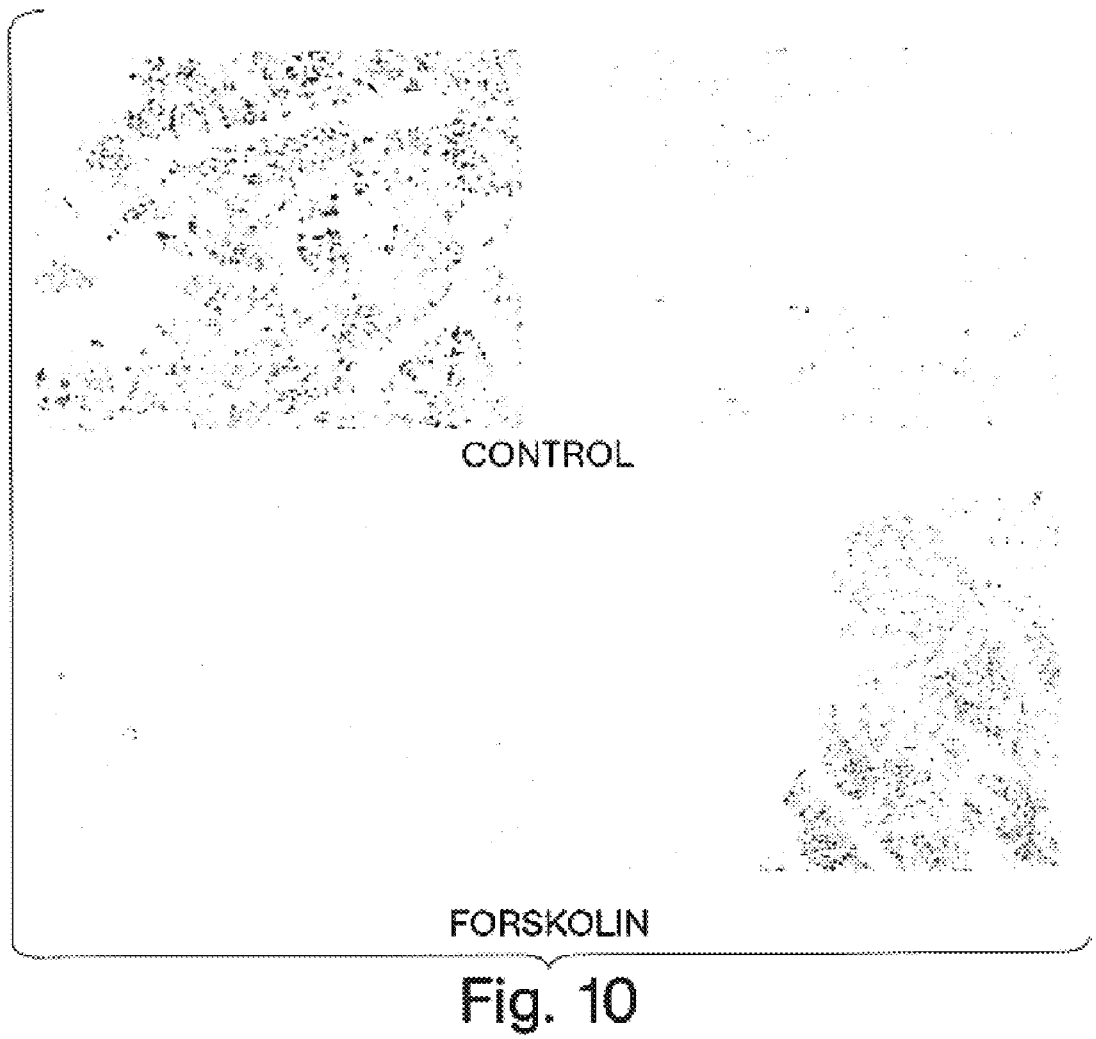
FIG. 10 shows Xgal staining (reflecting Hh pathway activation) of subcutaneous tumors, showing lower Xgal staining in forskolin-treated tumor.

To determine whether Hh signaling inhibitors can inhibit tumor growth in vivo, medulloblastoma cells from ptc-1 knockout mice were transplanted subcutaneously into athymic ("nude") mice. After allowing time for the tumor cells to grow at the injection site, the transplanted mice were divided into groups, and treated with either control vehicle, or cAMP agonist drugs. In one set of experiments, tumors were infused with either H-forskolin, or water as a control. After several days of drug infusion, the mice were sacrificed, and the tumors were sectioned for histology. The transplanted medulloblastoma cells from the ptc knockout mice contain a lacZ transgene (encoding $\beta$-galactosidase), the expression of which is induced by Hh signaling. Therefore, the level of $\beta$-galactosidase in these cells indicates their level of 1Hh signaling. Thus, in order to determine how effectively the infused drug inhibited Hh signaling in the tumor, the tumor sections were stained for $\beta$-galactosidase activity using the substrate Xgal, which stains expressing cells blue. Most of the tumors that received H-forskolin showed reduced Xgal staining, compared to control tumors. For example, FIG. 10 shows Xgal staining of two tumors each after infusion of control (water) or H-forskolin (note, in the forskolin-treated tumor that shows some Xgal staining, the empty half of the picture in fact contains cells, but these cells are Xgal-negative). These results suggest that Hh inhibitors can inhibit the Hh pathway in tumor cells in vivo.

Figure 11:
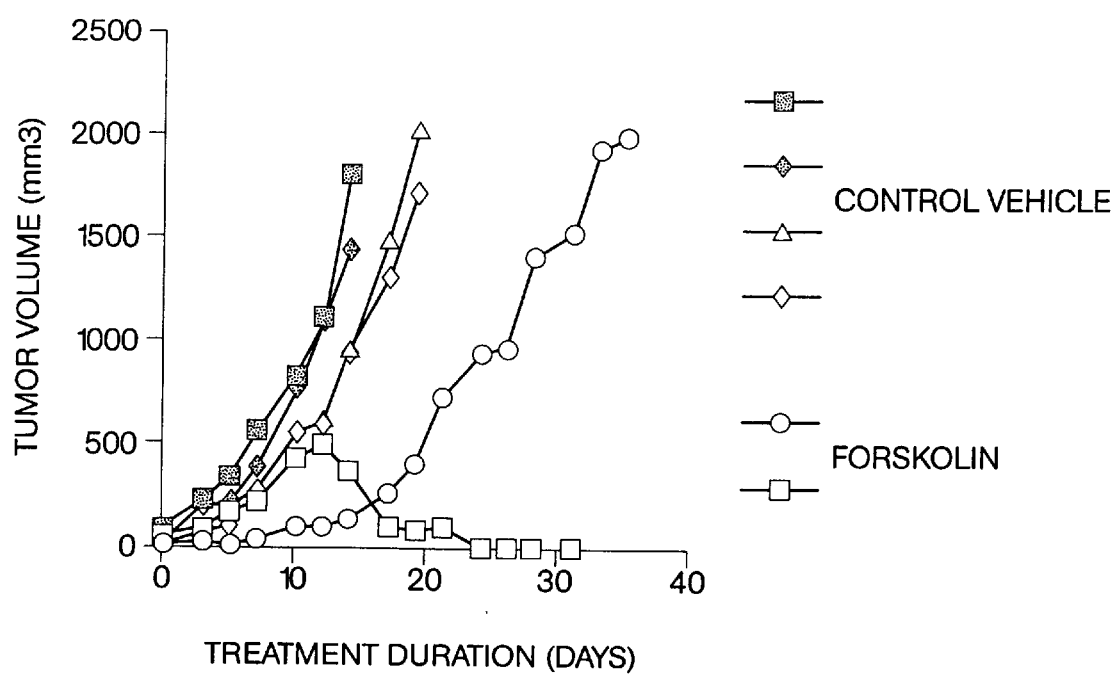
FIG. 11 depicts growth of subcutaneous-transplanted medulloblastoma tumors +/−forskolin treatment. Tumor volumes for individual mice are shown.
Figure 12:
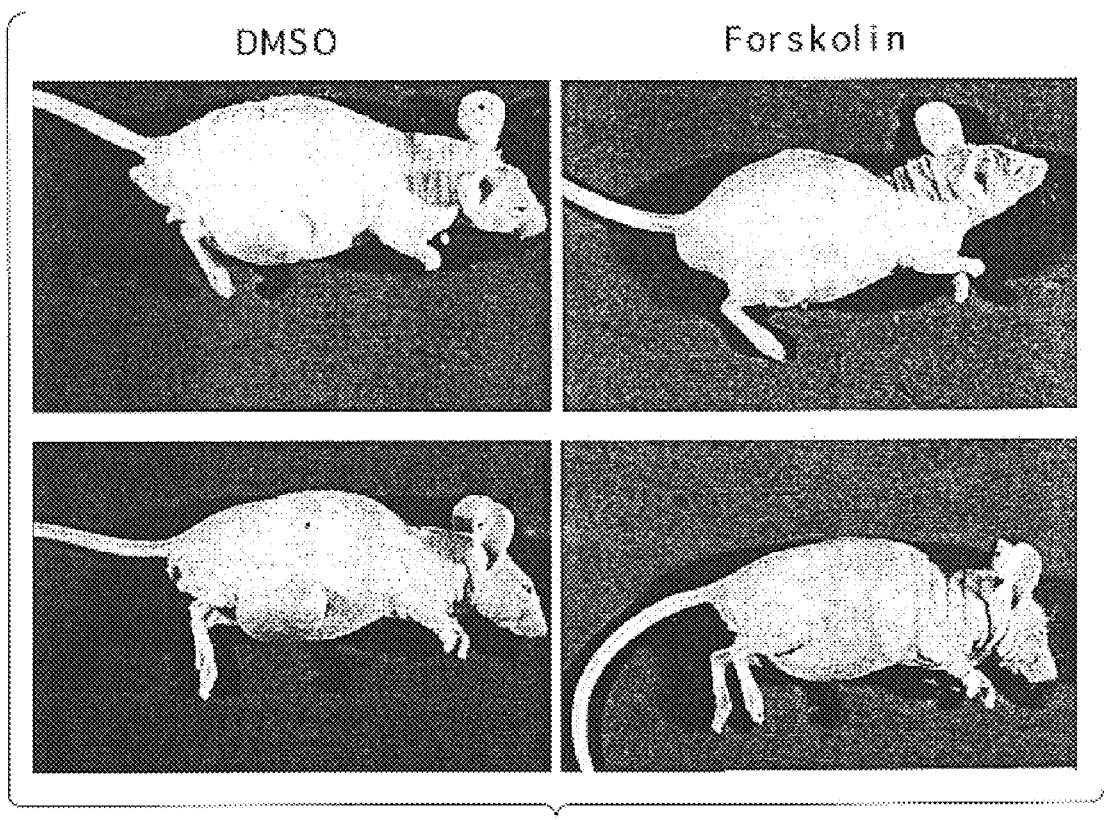
FIG. 12 depicts tumor sizes in mouse models.
Figure 13:
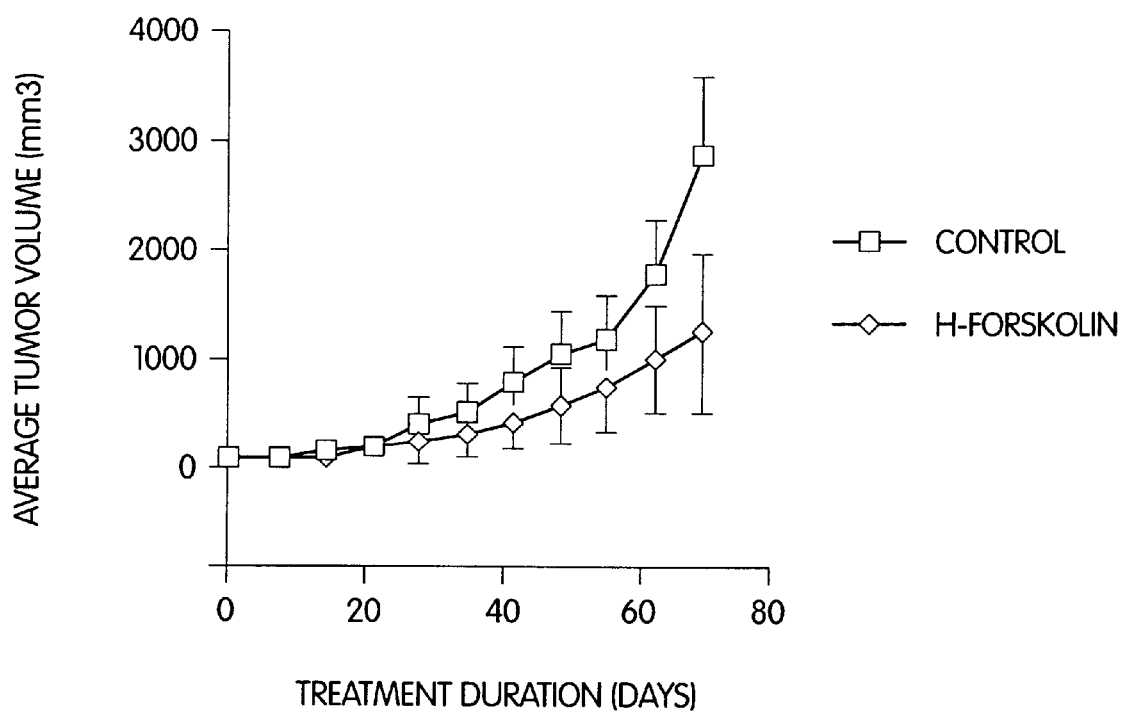
FIG. 13 presents growth of subcutaneous-transplanted medulloblastoma −/+ systemic forskolin. Average tumor volumes for each group are shown (four mice per group).

In order to determine whether Hh pathway inhibitors can inhibit tumor growth in vivo, cAMP agonists were administered to mice that, as above, had subcutaneous medulloblastoma tumors. In one experiment, one group of mice received daily intraperitoneal injections of forskolin, while control mice received equivalent injections of vehicle (DMSO). The volumes of the tumors were regularly determined by measuring tumor dimensions with a caliper. In the mice treated with DMSO control, the tumors grew much more rapidly than in the mice treated with forskolin. All of the control (DMSO) mice needed to be sacrificed within three weeks because the tumors reached an excessive size, while the tumors in the forskolin-treated mice did not grow excessively large for over for weeks (see FIGS. 11, 12). In one of the forskolin-treated mice, the tumor regressed, disappeared, and has not reappeared in over 60 days. In a similar experiment, H-forskolin or control vehicle was administered systemically to mice continuously, via an osmotic minipump that was implanted subcutaneously (and replaced regularly). Again in this experiment (FIG. 13), tumor size was smaller in the H-forskolin-treated mice than in the control mice. Together, these experiments suggest that inhibition of the Hh pathway, via cAMP agonist drugs, is an appropriate therapeutic approach for Hh pathway-based tumors.

Figure 14:
FIG. 14 presents tissue samples from newborn mice treated with forskolin.
Figure 14:

Topical application of forskolin on newborn Ptc-lacZ mice led to a decrease of hair density and abnormalities of hair follicle structure. This effect may be due to the inhibition of the Hh pathway by forskolin, as the Hh pathway plays a critical role in hair follicle development (FIG. 14). Postnatal day 2 mouse pups were used for this experiment. For each pup, 5 µl of DMSO or forskolin in DMSO (5 mM) was applied on the center of the back using a micro-pipette tip. The same procedure is repeated twice, with a total of 15 µt compound applied each time. The procedure was performed on the same animal twice a day for a period of 7 days. The pups were then sacrificed and the skin was taken from the applied area for histology analysis. H&E staining was performed on the paraffin embedded sections.

Figure 15:
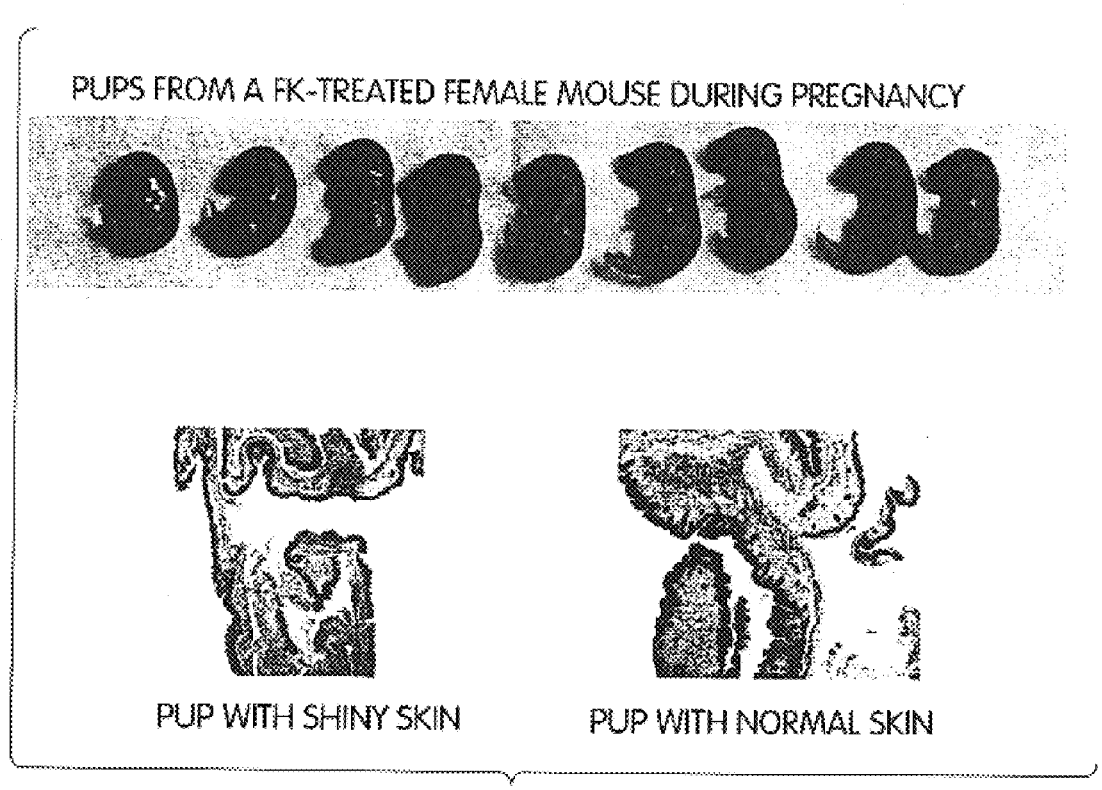
FIG. 15 shows pups from a forskolin-treated pregnant mouse, and samples of skin from the pups.

Injection of a pregnant female mouse with forskolin caused severe disruption of hair development in the fetus. Some fetuses had very shiny skin and histology analysis showed great reduction of the number of hair follicles, as shown in FIG. 15. For these experiments, 20 µl of forskolin in DMSO (50 mM) was injected into a pregnant female mouse daily for E14.5 to E17.5 intraperitoneally. The mouse was sacrificed at E17.5 and the fetuses were removed for gross inspection. The skin from each fetus was processed for H&E staining.

Figure 16:
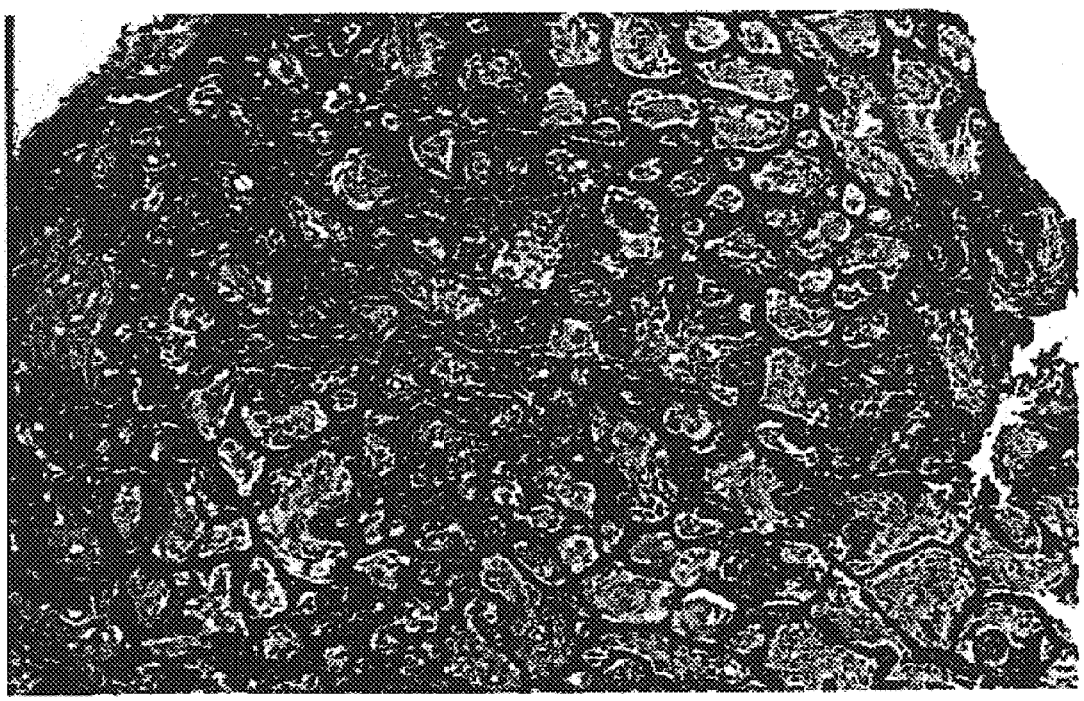
FIG. 16 displays tissue from mouse basal cell carcinoma (BCC).
Figure 17:
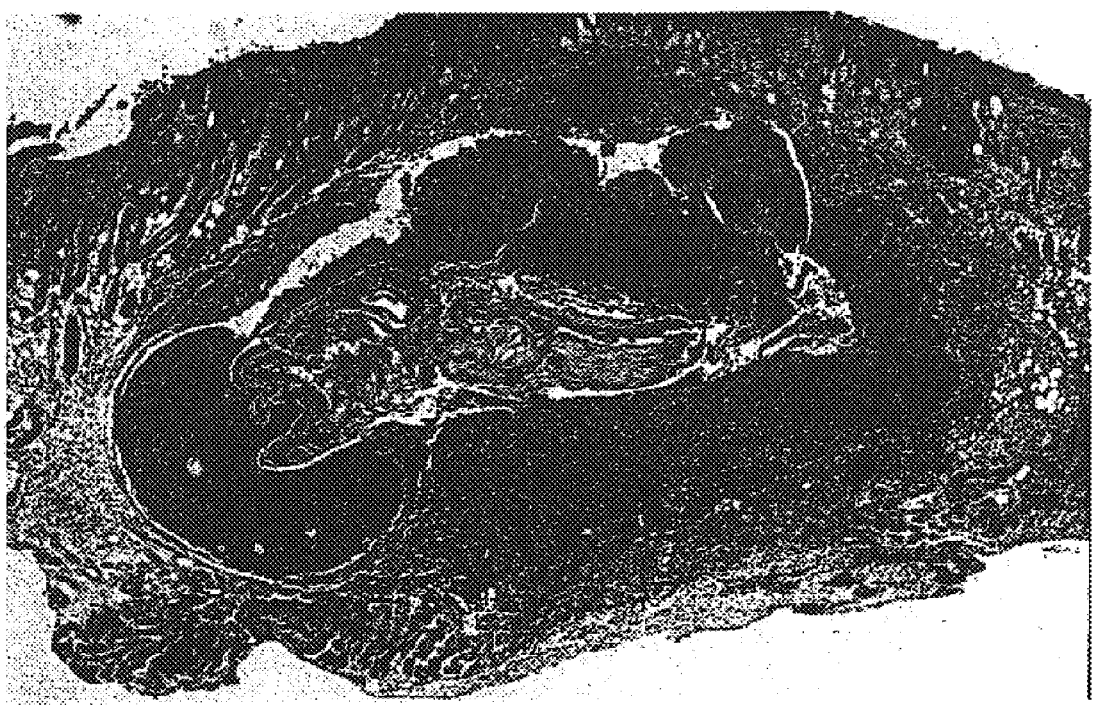
FIGS. 17 and 18 show mouse BCC tissue after treatment with forskolin, a cAMP agonist.
Figure 18:
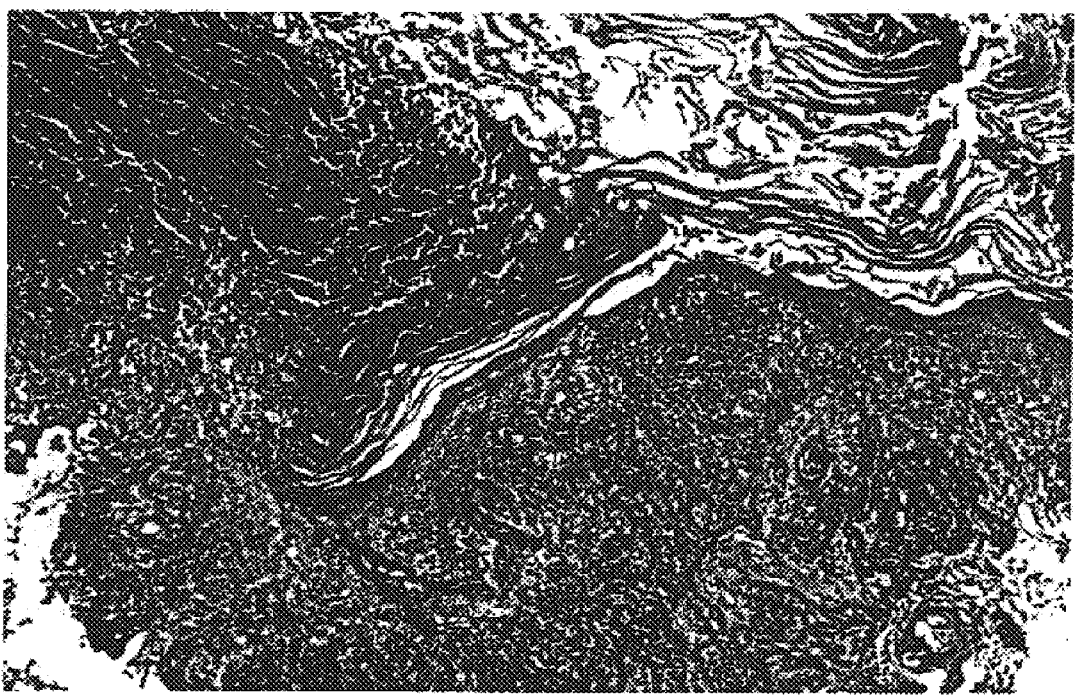

Experiments were conducted to determine the effect of cAMP elevating agents on basal cell carcinoma tissue. A solution of forskolin (50 mM) in ethanol was diluted 1:2 with cremophor (resulting in 50% ethanol/50% cremophor), then diluted 1:5 with PBS or normal saline (resulting in final 10% ethanol/10% cremophor/80% PBS or saline. The solution was administered by subcutaneous injection at different sites near the tumor (e.g., within a few millimeters of the margin), but not into the tumor itself. Treatment continued once a day every 24 hours for 21 days, 1 µl compound/g weight. After treatment, tumor size was measured, and the tumor was removed and analyzed by histology to determine morphological changes. Untreated BCC tissue is depicted in FIG. 16, and forskolin-treated tissue is depicted in FIGS. 17–18. White regions represent areas of tumor shrinkage and/or cell death.

In addition to the specific agents mentioned above, other agents that may be effective Hh tumor antagonists include, but are not limited to: pituitary adenylyl cyclase-activating polypeptide (PACAP), gastric inhibitory peptide (GIP), peptide-YY (PYY), glucagon-like peptide (GLP-1), secretin, vasoactive intestinal peptide (VIP), parathyroid hormone-related peptide (PTHrP), corticotropin-releasing hormone/corticotropin-releasing factor (CRH/CRF), and calcitonin gene-related peptide (CGRP); the neurotransmitters serotonin, epinephrine, dopamine, histamine, and vasopressin (or surrogate agonists of the receptors for these agents that elevate intracellular cAMP, or antagonists of the receptors for these agents that reduce intracellular cAMP); and agents that regulate intracellular cAMP by regulating the activity of phosphodiesterases.

Figure 19:
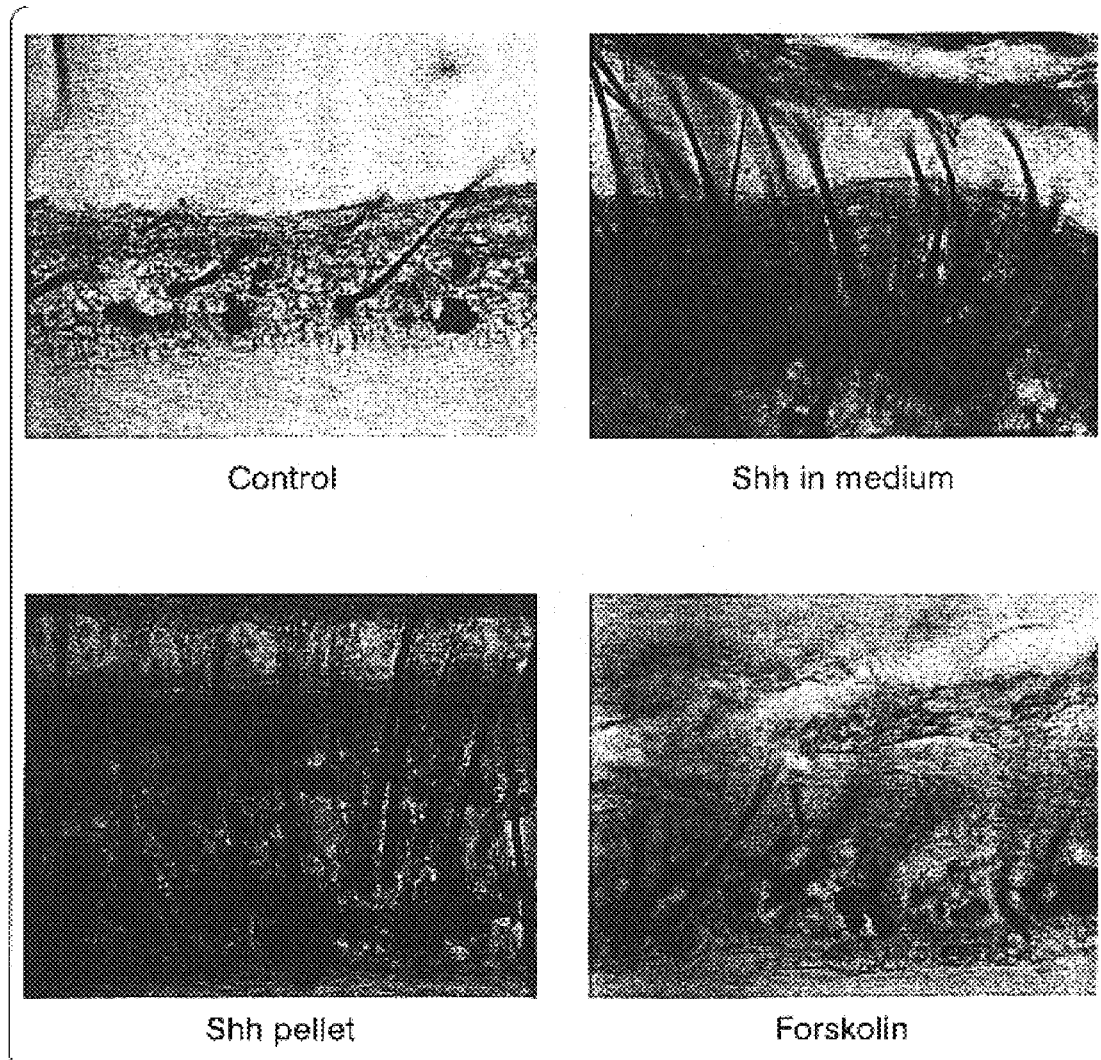
FIG. 19 depicts results of providing intradermal applications of Shh or forskolin to mouse skin.

FIG. 19 depicts hydron pellet implantation into 3-day mouse ptc-1 lacZ skin punches after 8 days of culture. Ethanol, hydron polymer, and Shh or forskolin in PBS, respectively, were mixed according to the manufacturer's instructions, poured in 2 mm pellet casts and dried/UV-irradiated over night. Alternatively, 3 mg/ml of octylated Shh protein was added to the culture medium (on day 1, 3 and 5) for the medium control as well as the forskolin-pellet implant. 3-day-old skin was harvested from the backs of mouse pups transgenic for ptc-1 lacZ, as identified by lacZ reporter detection using tails, by standard procedures. 6 mm skin punches were taken using Miltex skin punches and incubated for 60 min. Pellets were inserted by carefully separating the dermal from the epidermal layer using forceps. Cultures were grown for 8 days, fixed in lacZ fixative according to standard protocols, rinsed and stained for lacZ over night at 37° C.

Results: (A) Untreated control, showing a small number of short hairs. (B) Skin punches treated with the signaling protein sonic hedgehog (Shh) by addition to the culture medium display an increased rate of follicle induction but normal spatial arrangement of hairs as compared to the control. Hair length and thickness of the dermis thickness are increased as well. Ptc-lacZ, a reporter gene indicative of Shh signaling is induced in follicular as well as basal cells (blue stain), although partially obscured by melanin. (C) Implantation of pellets loaded with Shh leads to significantly increased induction of hair follicles, hair length and pigmentation, as well as increased thickness of the dermis. Note the highly localized area of follicle induction, corresponding to the area adjacent to bead insertion. The lacZ signal in hair follicles is almost completely obscured by melanin. Basal cells express ptc-lacZ in response to Shh. (D) Implantation of pellets loaded with forskolin, a known Shh antagonist, leads to a reduction of hair follicles, hair length, pigmentation and dermis thickness to levels comparable to the control (A), even when Shh is supplied with the culture medium (compare D to B).

Equivalents

Those skilled in the art will be recognized, or be able to ascertain using no more than routine experimentation, many equivalents to the specific embodiments of the invention described herein. Such equivalents are intended to be encompassed by the following claims.

We claim:

1. A method for inhibiting an altered growth state of a cell having a ptc loss-of-function phenotype, or a smoothened gain-of-function phenotype, comprising contacting the cell with a composition including at least one cAMP agonist.

2. The method of claim 1, wherein at least one cAMP agonist activates adenylate cyclase.

3. The method of claim 1, wherein the least one cAMP agonist is a cAMP analog.

4. The method of claim 1, wherein at least one cAMP agonist is a cAMP phosphodiesterase inhibitor.

5. The method of claim 1, wherein the composition inhibits ptc loss-of-function, or smoothened gain-of-function mediated signal transduction with an $ED_{50}$ of 1 mM or less.

6. The method of claim 1, wherein the composition inhibits ptc loss-of-function, or smoothened gain-of-function mediated signal transduction with an $ED_{50}$ of 1 µM or less.

7. The method of claim 1, wherein the composition inhibits ptc loss-of-function, or smoothened gain-of-function mediated signal transduction with an $ED_{50}$ of 1 mM or less.

8. The method of claim 1, wherein the tissue is contacted with the composition in vitro.

9. The method of claim 1, wherein the tissue is contacted with the composition in vivo.

10. The method of claim 1, wherein the composition includes forskolin or a derivative thereof.

11. The method of claim 1, wherein the composition is administered as part of a therapeutic or cosmetic application.

12. The method of claim 11, wherein the therapeutic or cosmetic application is selected from the group consisting of regulation of neural tissues, bone and cartilage formation and repair, regulation of spermatogenesis, regulation of smooth muscle, regulation of lung, liver and other organs arising from the primitive gut, regulation of hematopoietic function, or regulation of skin and hair growth.

13. A method for treatment or prophylaxis of basal cell carcinoma, comprising administering a composition including a cAMP agonist to a patient in need thereof in an amount sufficient to inhibit progression of basal cell carcinoma.

14. A method for inhibiting an altered growth state of a cell having a ptc loss-of-function or a smoothened gain-of-function comprising:

determining the phenotype of the cell; and if the phenotype is ptc loss-of-function, or a smoothened gain-of-function phenotype, treating the cell with a cAMP agonist in an amount sufficient to inhibit the altered growth state of the cell.

* * * * *